(12) United States Patent
Fukuma et al.

(10) Patent No.: US 7,641,338 B2
(45) Date of Patent: Jan. 5, 2010

(54) FUNDUS OBSERVATION DEVICE

(75) Inventors: Yasufumi Fukuma, Tokyo (JP);
Hiroyuki Aoki, Tokyo (JP); Hisashi Tsukada, Tokyo (JP); Tsutomu Kikawa, Tokyo (JP)

(73) Assignee: Kabushiki Kaisha Topcon, Itabashi-Ku (JP)

( * ) Notice: Subject to any disclaimer, the term of this patent is extended or adjusted under 35 U.S.C. 154(b) by 0 days.

(21) Appl. No.: 11/689,090

(22) Filed: Mar. 21, 2007

(65) Prior Publication Data

US 2007/0222946 A1 Sep. 27, 2007

(30) Foreign Application Priority Data

Mar. 24, 2006 (JP) ............... 2006-082121

(51) Int. Cl.
*A61B 3/14* (2006.01)
*A61B 3/10* (2006.01)

(52) U.S. Cl. ...................... 351/206; 351/221

(58) Field of Classification Search ......... 359/205–206, 359/221; 354/62
See application file for complete search history.

(56) References Cited

U.S. PATENT DOCUMENTS

| 5,321,501 | A | 6/1994 | Swanson et al. |
| 5,760,781 | A | 6/1998 | Kaufman et al. |
| 5,975,697 | A | 11/1999 | Podoleanu et al. |
| 6,179,421 | B1 | 1/2001 | Pang |
| 6,293,674 | B1 | 9/2001 | Huang et al. |
| 2004/0036838 | A1 | 2/2004 | Podoleanu et al. |
| 2004/0066489 | A1 | 4/2004 | Benedikt et al. |
| 2005/0270486 | A1 | 12/2005 | Teiwes et al. |
| 2007/0159595 | A1* | 7/2007 | Fukuma et al. ............. 351/206 |
| 2007/0188707 | A1* | 8/2007 | Nanjo ....................... 351/206 |

FOREIGN PATENT DOCUMENTS

| EP | 0 621 546 | 10/1994 |
| EP | 1 527 731 | 5/2005 |
| JP | 2003-000543 | 1/2003 |
| JP | 2004-350849 | 12/2004 |
| JP | 2005-241464 | 9/2005 |

OTHER PUBLICATIONS

European Search Report mailed Mar. 31, 2008, issued in EP 07 00 5798.

* cited by examiner

*Primary Examiner*—Scott J Sugarman
*Assistant Examiner*—Dawayne A Pinkney
(74) *Attorney, Agent, or Firm*—Edwards Angell Palmer & Dodge LLP

(57) ABSTRACT

Image forming part 220 forms a 2-dimensional image of the surface of the fundus oculi Ef (fundus oculi image) and a tomographic image of the fundus oculi Ef. The fundus oculi image 212a and the tomographic image Ga captured at the first examination time and the fundus oculi image 212b and the tomographic image Gb captured at the second examination time are stored in an image storage part 212. Position information generating part 214 generates the position information 213a indicating the position of the tomographic image Ga in the fundus oculi image 212a and the position information 213b indicating the position of the tomographic image Gb in the fundus oculi image 212b. The generated position information 213a and 213b are stored in information storage part 213. Image processing part 230 adjusts the position between the tomographic images Ga and Gb based on such position information 213a and 213b.

7 Claims, 14 Drawing Sheets

FUNDUS OBSERVATION DEVICE

BACKGROUND OF THE INVENTION

1. Field of the Invention

The present invention relates to a fundus observation device, for observing the state of the fundus oculi of an eye.

2. Description of the Related Art

As a fundus observation device, conventionally a fundus camera has been widely used. FIG. 13 shows one example of the appearance of a conventional fundus camera in general, and FIG. 14 shows one example of an optical system composition to be internally accommodated therein (e.g. JP Patent laid-open No. 2004-350849). Furthermore, "observation" is intended to include at least a case in which produced fundus images are observed (fundus observations with the naked eye may be included).

First, referring to FIG. 13, an explanation is made regarding the appearance of a conventional fundus camera 1000. This fundus camera 1000 is provided with a platform 3 mounted on a base 2 slidably in the front and rear, right and left (horizontal direction) directions. On this platform 3, an operation panel 3a and a control lever 4 are installed for an examiner to conduct various operations.

The examiner may place the platform 3 on the base 2 to be moved 3-dimensionally by operating the control lever 4. On the top of the control lever 4, an operation button 4a is installed to be pressed down to obtain fundus oculi images.

On the base 2, a post 5 is installed standing upwards. On the post 5, a jaw rest 6 where the jaw of a patient is to be rested and an external fixation lamp 7 as a light source for fixing an eye E are provided.

On the platform 3, a main body part 8 is installed to accommodate various optical systems or control systems of the fundus camera 1000. Furthermore, the control system may be installed inside the base 2 or the platform 3, etc., or in an external device such as a computer, etc. connected to the fundus camera 1000.

On the side of the eye E of the main body part 8 (the left side of the page in FIG. 13), an objective lens part 8a disposed opposite the eye E is installed. Also, on the examiner's side of the main body part 8 (the right side of the page in FIG. 13), an objective lens part 8b for observing the fundus oculi of the eye E with the naked is installed.

Furthermore, connected to the main body part 8 is a still camera 9 for producing a still image of a fundus oculi of the eye E and an imaging device 10 such as a TV camera, etc. for producing still images or moving images of a fundus oculi. The still camera 9 and the imaging device 10 are formed removably with respect to the main body part 8.

As a still camera 9, in accordance with various conditions such as the purpose of an examination or the saving method of produced images, etc., a digital camera equipped with imaging elements such as CCD (Charge Coupled Device) or CMOS (Complementary Metal Oxide Semiconductor), a film camera, and an instant camera, etc. may interchangeably be used when it is appropriate. The main body part 8 is equipped with a mounting part 8c for interchangeably mounting such a still camera 9.

If the still camera 9 or the imaging device 10 is for taking digital images, the image data of the produced fundus image may be sent to a device such as a computer, etc. connected to the fundus camera 1000 and be observed as a fundus image by being displayed on the display. Also, the image data can be sent to an image storing device connected to the fundus camera 1000 to compile a database and be used as electronic data for creating medical charts, etc.

Furthermore, on the examiner's side of the main body part 8, a touch panel monitor 11 is installed. On this touch panel monitor 11, fundus images of the eye E created based on the video signals output from the still camera 9 (a digital method thereof) or the imaging device 10 are displayed. Moreover, on the touch panel monitor 11, the 2-dimensional coordinate system with the center of the screen as the origin is displayed overlapped with a fundus image. When the screen is touched by the examiner, the coordinate value corresponding to the touched position is displayed.

Next, referring to FIG. 14, a composition of an optical system of the fundus camera 1000 is described. The fundus camera 1000 is provided with an illuminating optical system 100 to light the fundus oculi Ef of an eye E, an imaging optical system 120 to guide the fundus reflection light of the illumination light to the eyepiece part 8b, a still camera 9, and an imaging device 10.

The illuminating optical system 100 comprises: an observation light source 101, a condenser lens 102, an imaging light source 103, a condenser lens 104, an exciter filter 105 and 106, a ring transparent plate 107, a mirror 108, a liquid crystal display (LCD) 109, an illumination diaphragm 110, a relay lens 111, an aperture mirror 112, and an objective lens 113.

The observation light source 101 consists of a halogen lamp, etc. and emits continuous light for observing the fundus. The condenser lens 102 is an optical element that converges the continuous light (observation illumination light) emitted by the observation light source 101 and substantially evenly irradiates the observation illumination light to the fundus oculi.

The imaging light source 103 consists of a xenon lamp, etc. to be flashed when producing fundus oculi Ef images. The condenser lens 104 is an optical element that converges the flash light (imaging illumination light) emitted by the imaging light source 103 and irradiates the fundus oculi Ef evenly with the imaging illumination light.

The exciter filters 105 and 106 are the filters to be used when fluorography of images of a fundus oculi Ef takes a place. The exciter filters 105 and 106 respectively can be inserted and removed on the optical path by a drive mechanism such as a solenoid, etc. The exciter filter 105 is disposed on the optical path in the event of FAG (fluorescein angiography). Whereas, the exciter filter 106 is disposed on the optical path in the event of ICG (indocyanine green angiography). Furthermore, when color images are being obtained, both exciter filters 105 and 106 are retracted from the optical path.

The ring transparent plate 107 is disposed in a conjugating location with a pupil of the eye E, and is equipped with a ring transparent part 107a taking an optical axis of the illuminating optical system 100 as a center. The mirror 108 reflects the illumination light emitted by the observation light source 101 or by the imaging light source 103 in the direction of the optical axis of the imaging optical system 120. The LCD 109 displays a fixation target (not illustrated) for fixing the eye E.

The illumination diaphragm 110 is a diaphragm member to shut out a part of the illumination light for flare prevention, etc. This illumination diaphragm 110 is composed movably in the light axial direction of the illuminating optical system 100, and is thus capable of changing the illuminating region of the fundus oculi Ef.

The aperture mirror 112 is an optical element to combine an optical axis of the illuminating optical system 100 and an optical axis of the imaging optical system 120. In the center region of the aperture mirror 112 an aperture part 112a is opened. The light axis of the illuminating optical system 100 and the light axis of the imaging optical system 120 are to be crossed at a substantially central location of this aperture part 112a. The objective lens 113 is installed in the objective lens part 8a of the main body part 8.

The illuminating optical system 100 having such a composition illuminates a fundus oculi Ef in the following manner. First, the observation illumination light is emitted when the observation light source 101 is lit during fundus observation. This observation illumination light irradiates the ring transparent plate 107 through the condenser lenses 102 and 104. (The exciter filters 105 and 106 are removed from the optical path.) The light passed through the ring transparent part 107a of the ring transparent plate 107 is reflected by the mirror 108 and is reflected along the optical axial direction of the imaging optical system 120 due to the aperture mirror 112 through the LCD 109, the illumination diaphragm 110 and the relay lens 111. The observing illumination light reflected by the aperture mirror 112 advances in the optical axial direction of the imaging optical system 120 and is converged by the objective lens 113, to be made incident onto the eye E, and illuminates the fundus oculi Ef.

Then, the ring transparent plate 107 is disposed in a conjugating location with the pupil of the eye E, and on the pupil a ring shaped image of the entering observation illumination light is formed. The fundus reflection light of the entered observation illumination light is to be emitted from the eye E through a central dark part of the ring image on the pupil. As described, it is to protect the effect of observing illumination light entering the eye E with respect to the fundus reflection light of the observing illumination light.

On the other hand, when imaging the fundus oculi Ef, flush light is emitted from the imaging light source 103 and the imaging illumination light is irradiated onto the fundus oculi Ef through the same path. In the event of photofluographing, either the exciter filter 105 or the exciter filter 106 is disposed selectively on the optical path depending on whether FAG imaging or ICG imaging is carried out.

Whereas, imaging optical system 120 comprises: an objective lens 113, an aperture mirror 112 (an aperture part 112a thereof), an imaging diaphragm 121, a barrier filter 122 and 123, a variable magnifying lens 124, a relay lens 125, an imaging lens 126, a quick return mirror 127 and an imaging media 9a. Herein, the imaging media 9a is an arbitrary imaging media (image pick-up elements such as CCD, camera film, instant film, etc.) used for a still camera 9.

The fundus reflection light of the illumination light, emitted through the central dark part of the ring shaped image formed on the pupil from the eye E, enters the imaging diaphragm 121 through the aperture part 112a of the aperture mirror 112. The aperture mirror 112 reflects cornea reflection light of the illumination light and acts so as not to mix the cornea reflection light into the fundus reflection light made incident onto the imaging diaphragm 121. As a result, the generation of flare on the observation images and/or produced images is prevented.

The imaging diaphragm 121 is a plate shaped member at which plural circular light transparent parts of different sizes are formed. The plural light transparent parts constitute different diaphragms with different diaphragm values (F value), and are to be disposed alternatively on the optical path by a drive mechanism (not illustrated herein).

The barrier filters 122 and 123 can be inserted and removed on the optical path by a drive mechanism such as a solenoid, etc. In the event of FAG imaging, the barrier filter 122 is disposed on the optical path while in the event of ICG imaging the barrier filter 123 is inserted onto the optical path. Furthermore, when producing color images the barrier filters 122 and 123 are to be retracted from the optical path.

The variable magnifying lens 124 is to be movable in the light axial direction of the imaging optical system 120 by a drive mechanism (not illustrated herein). This makes it possible to change the magnifying ratio of an observation and the magnifying ratio in imaging, and to focus images of a fundus oculi. The imaging lens 126 is a lens to focus the fundus reflection light from an eye E on the imaging media 9a.

The quick return mirror 127 is disposed rotatably around a rotary shaft 127a by a drive mechanism not illustrated herein. In the event of imaging a fundus oculi Ef with the still camera 9, the fundus reflection light is supposed to be guided to the imaging media 9a by springing up the quick return mirror 127 that is obliquely mounted on the optical path. Whereas, in the event of imaging a fundus oculi with an imaging device 10 or of observing the fundus oculi with the naked eye of the examiner, the quick return mirror 127 is to be obliquely mounted on the optical path to upwardly reflect the fundus reflection light.

The imaging optical system 120 is further provided, for guiding the fundus reflection light reflected by the quick return mirror 127, with a field lens 128, a switching mirror 129, an eyepiece 130, a relay lens 131, a reflection mirror 132, an imaging lens 133 and an image pick up element 10a. The image pick up element 10a is an image pick up element such as CCD, etc. installed internally in the imaging device 10. On the touch panel monitor 11 a fundus oculi image Ef' imaged by the image pick up element 10a is be displayed.

The switching mirror 129 is to be rotatable around the rotary shaft 129a as well as the quick return mirror 127. This switching mirror 129 is obliquely disposed on the optical path during observation with the naked eye and guides reflected light on the fundus oculi to the eyepiece 130.

Also, when a fundus image is formed by the imaging device 10, the switching mirror 129 is retracted from the optical path, and the fundus reflection light is guided toward an image pick-up element 10a. In this case, the fundus reflection light is directed toward a relay lens 131, is reflected by the mirror 132, and is focused on the image pick-up element 10a by the imaging lens 133.

Such a fundus camera 1000 is a fundus observation device to be used for observing the state of the surface of a fundus oculi Ef, that is, the retina. In other words, a fundus camera 1000 is a fundus observation device to obtain a 2-dimensional fundus oculi image when it sees the fundus oculi Ef from the corneal direction onto the eye E. On the other hand, in the deep layer of retina tissues such as the choroidea or sclera exist, technology for observing these deep layer tissues has been desired, but, in recent years, devices for observing these deep layer tissues have been practically implemented (e.g. JP Patent laid-open No. 2003-00543, JP Patent laid-open No. 2005-241464).

The fundus observation device disclosed in JP Patent laid-open No. 2003-00543 and JP Patent laid-open No. 2005-241464 are devices to which so called OCT (Optical Coherence Tomography) technology is applied. With such fundus observation devices, low coherence light is split into two, one of which (signal light) is guided to a fundus oculi and the other one (reference light) is guided to a given reference object, and this is a device to form tomographic images of the surface and the deep layer tissue of a fundus oculi, and to form the 3-dimensional image from the tomographic images, by detecting and analyzing the interference light obtained by overlaying the signal light that has reached the fundus oculi and the reference light that has been reflected by the reference object. Such devices are in general called a Fourier domain OCT.

The Fourier domain OCT is designed to form a tomographic image having a depth-wise cross-section along its scanning line by scanning and irradiating a signal light onto the fundus oculi. Such scanning of signal lights is referred to as a B-scan (see NEDO Workshop "Seeing (examining) inside the body from the 'window' of the human body, the fundus oculi"—Development of an ultra early diagnostic device for lifestyle-related diseases using the latest optical technologies (held on Apr. 25, 2005), Internet<URL: http://www.nedo.go.jp/informations/koubo/170627_2/besshi3.pdf>).

When forming a 3-dimensional image, a B-scan is performed along a plurality of scanning lines, and an interpolation process is applied to the resulting plurality of tomographic images for the generation of 3-dimensional image data. This 3-dimensional image data is referred to as volume data, voxel data, and so forth, as well as medical imaging diagnosis devices such as an X-ray CT device, which is image data in a form in which pixel data (e.g. luminance value and RGB value regarding brightness, contrasting density and color) is assigned to each voxel. A 3-dimensional image is displayed as a pseudo 3-dimensional image seen from a certain viewing angle obtained by rendering volume data.

Not limited to ophthalmology, a elapsed observation is common throughout the entire medical field for diagnosing the status of injury or sickness, therapeutic effects, and so forth. A elapsed observation is to undertake diagnostic evaluation by performing examinations repeatedly over a certain period and comparing the examination results thereof. In a elapsed observation, the changes over time in a region of interest are often seen by capturing images of a region of interest such as an affected area for a certain period and comparing those images.

Although images of the same site need to be captured repeatedly in an elapsed observation using images, it has been difficult to capture images of the same site in an examination of the fundus oculi using conventional fundus observation devices. That is, in order to capture images of the same site on each examination, an eye to be examined must be fixated in the same direction, which is difficult to do. In addition, it has also been a factor of making the capture of images of the same site difficult that pulsation or the like due to eye movement or the bloodstream causes the direction of an eye to change.

In particular, when comparing the tomographic images of a fundus oculi captured by an optical image measuring device, it has been difficult to determine from the images whether such tomographic images are images of the same site (the same cross-section) of the fundus oculi. In addition, it has also been difficult to recapture a tomographic image of the same cross-section as the tomographic image captured in the past. Therefore, it has been difficult to effectively and efficiently perform an elapsed observation.

The present invention is intended to solve the above mentioned problems, with the purpose of providing a fundus observation device capable of effectively and efficiently performing an elapsed observation using tomographic images of a fundus oculi.

SUMMARY OF THE INVENTION

In order to achieve the above purpose, the first aspect of the present invention is constructed as follows; a fundus observation device comprising: an image forming part including a first image forming part and a second image forming part, the first image forming part configured to form a 2-dimensional image of the surface of the fundus oculi of an eye based on optically captured data, a second image forming part configured to form tomographic, images of said fundus oculi based on data captured by an optical scan; a position information generating part configured to generate position information for said 2-dimensional image and said tomographic image which are formed substantially simultaneously, the position information indicating the position of the tomographic image in the 2-dimensional image; and an image processing part configured to adjust the position, based on said position information generated for said 2-dimensional image and said tomographic image which are formed substantially simultaneously and based on said position information generated for said 2-dimensional image and said tomographic image which are formed substantially simultaneously at a subsequent time, of said former tomographic image and said latter tomographic image.

Also, the second aspect of the present invention is constructed as follows; a fundus observation device comprising: an image forming part configured to form a tomographic image of a fundus oculi of an eye based on data captured by an optical scan, a position information generating part configured to generate the depth information indicating depth-wise position of the tomographic image based on the formed tomographic image, and an image processing part configured to adjust the position, based on said depth information generated for said tomographic image formed and said depth information generated for said tomographic image formed at a subsequent time, of said former tomographic image and said latter tomographic image depth-wise.

Also, the third aspect of the present invention is constructed as follows; a fundus observation device comprising: an image forming part configured to form a tomographic image of a fundus oculi of an eye based on data captured by an optical scan; an accumulated image generating part configured to generate a first and a second accumulated images by accumulating each of a first said tomographic image and a second said tomographic image formed on different examination dates and times in the direction of depth; an accumulated image displacement calculating part configured to perform calculations for displacement of the generated first accumulated image and second accumulated image; and an image position changing part configured to adjust the position, based on the calculated displacement, of said first tomographic image and said second tomographic image in the direction of the surface of said fundus oculi.

BRIEF DESCRIPTION OF THE DRAWINGS

FIG. 8 is a schematic diagram representing one example of scanning features of signal light in a preferred embodiment of the fundus observation device related to the present invention.

DETAILED DESCRIPTION OF THE REFERENCE EMBODIMENTS

Figure 13:
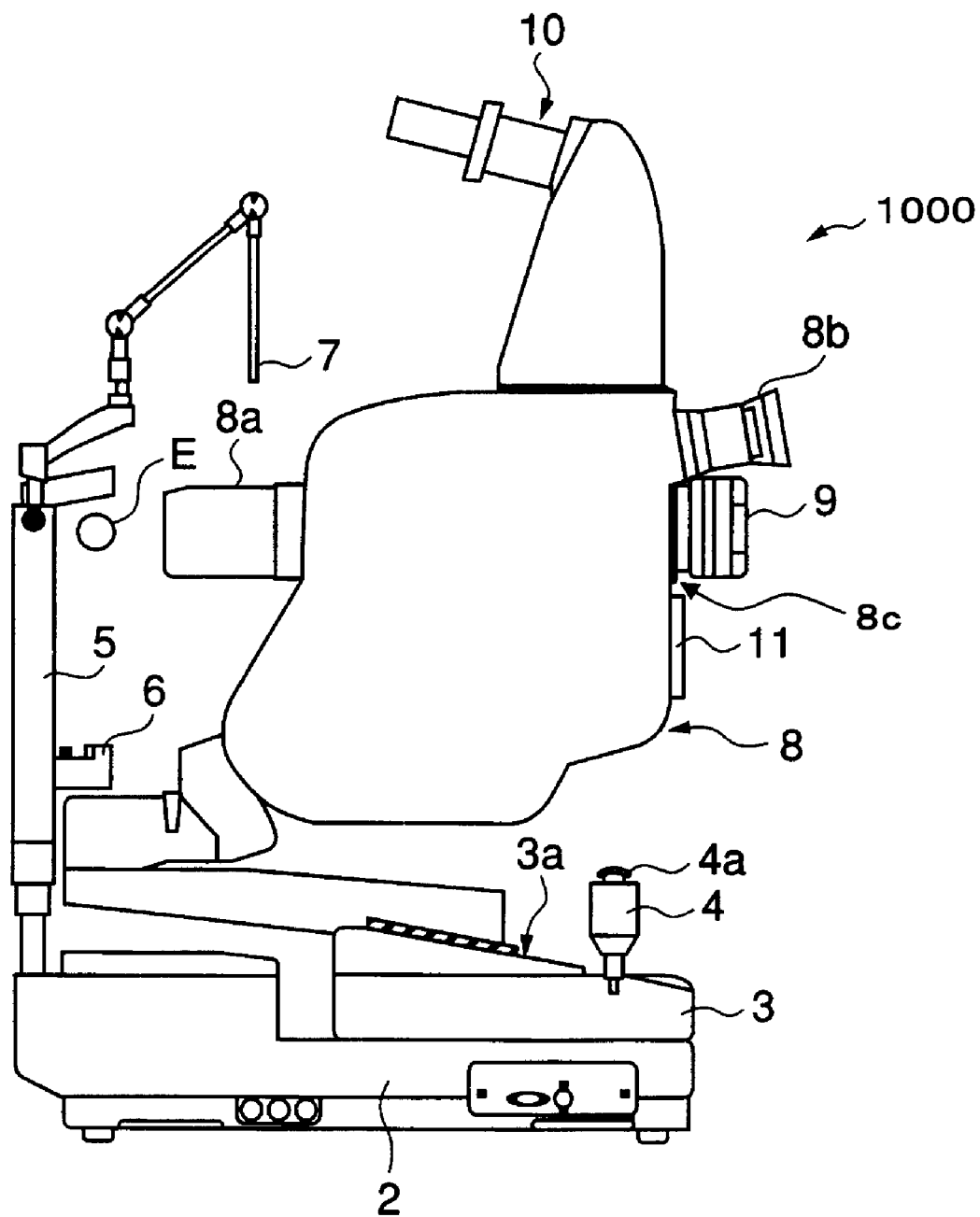
FIG. 13 is a schematic diagram showing one example of the appearance of a conventional fundus observation device (optical image measuring device).
Figure 14:
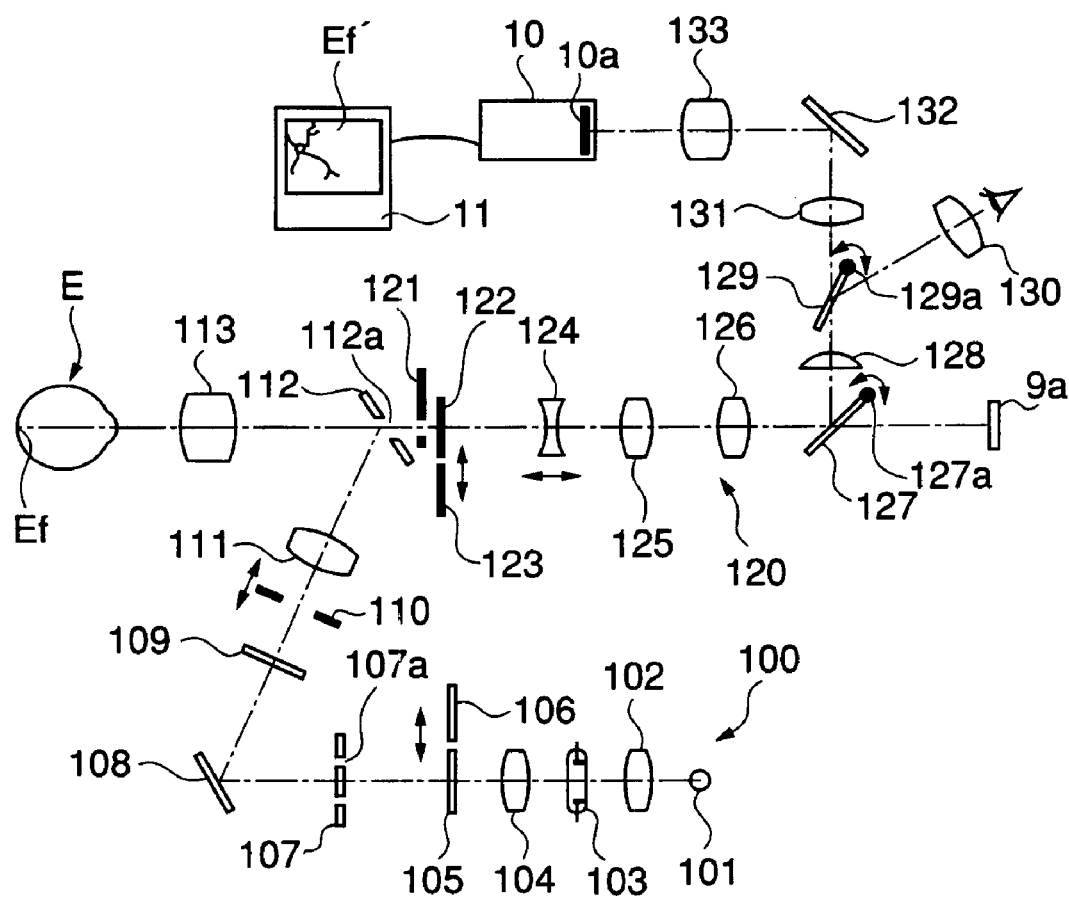
FIG. 14 is a schematic diagram representing one example of an internal constitution (an optical system constitution) of a conventional fundus observation device (fundus camera).

One example of favorable embodiments of a fundus observation device related to the present invention is described in detail referring to figures. Furthermore, for structural parts that are the same as conventional ones, the same symbols used in FIG. 13 and FIG. 14 are used.

Figure 1:
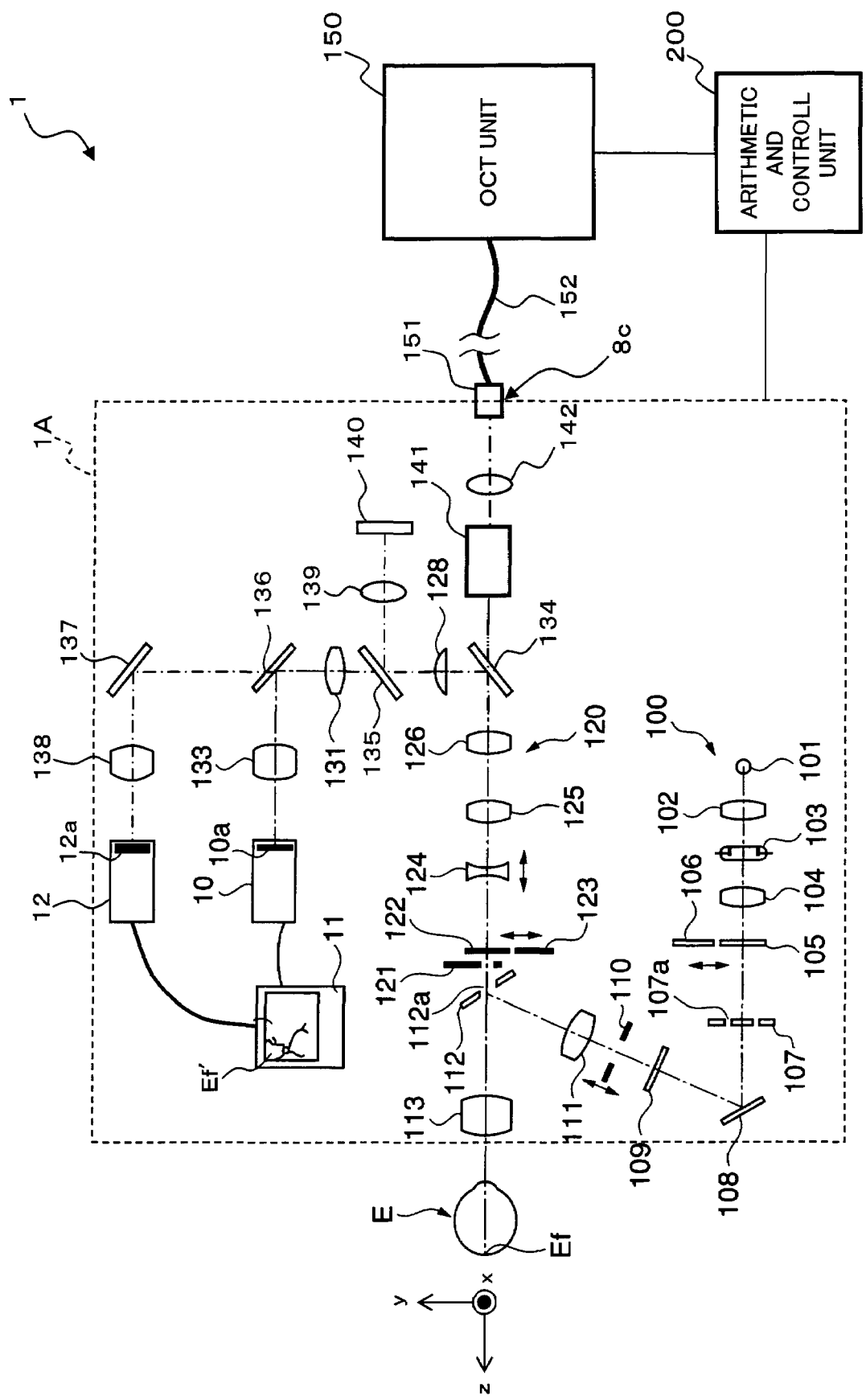
FIG. 1 is a schematic diagram representing one example of the entire constitution in a preferred embodiment of the fundus observation device related to the present invention.
Figure 2:
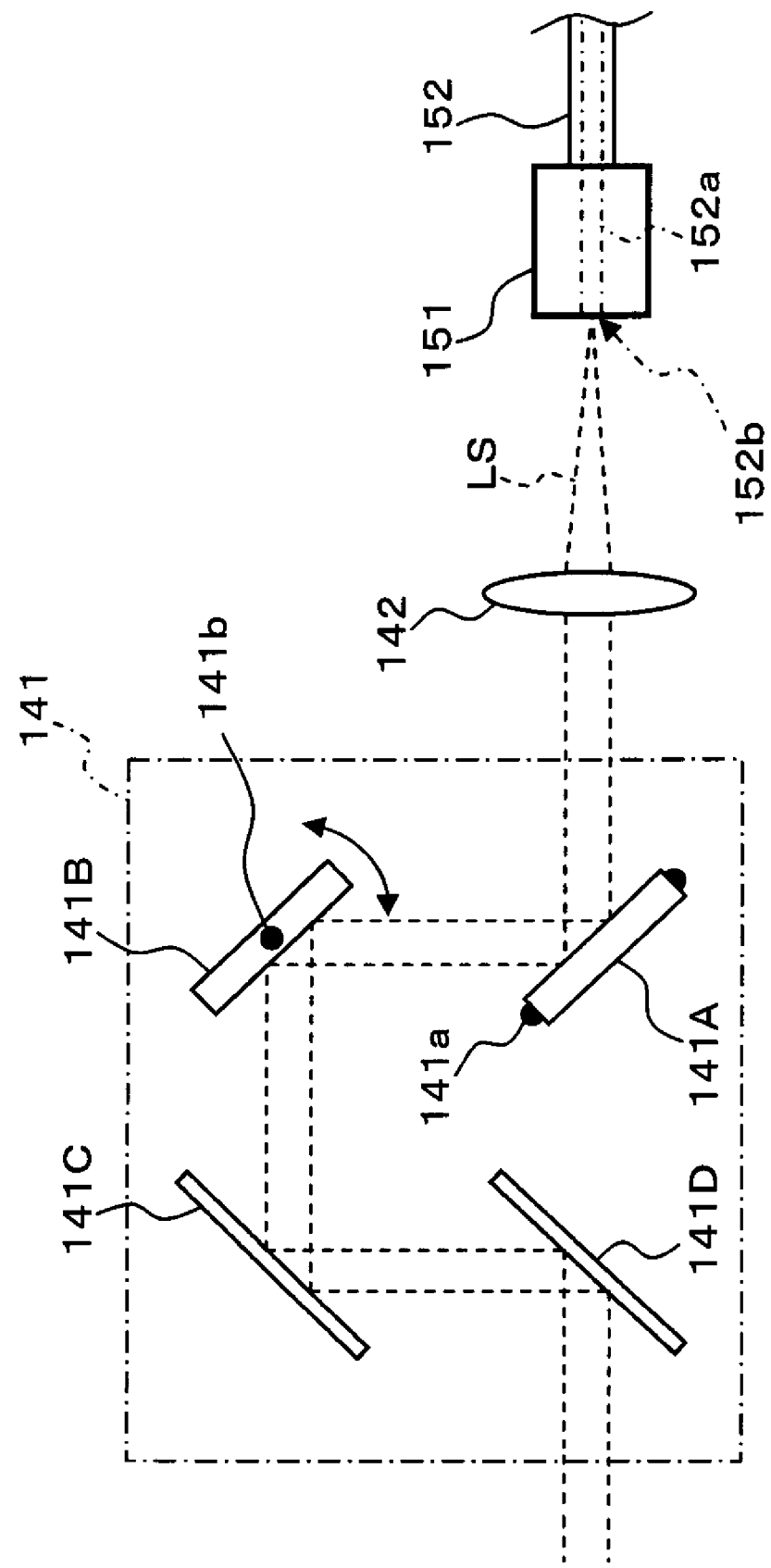
FIG. 2 is a schematic diagram representing one costitutional example of a scanning unit installed in a fundus camera unit in a preferred embodiment of the fundus observation device related to the present invention.
Figure 3:
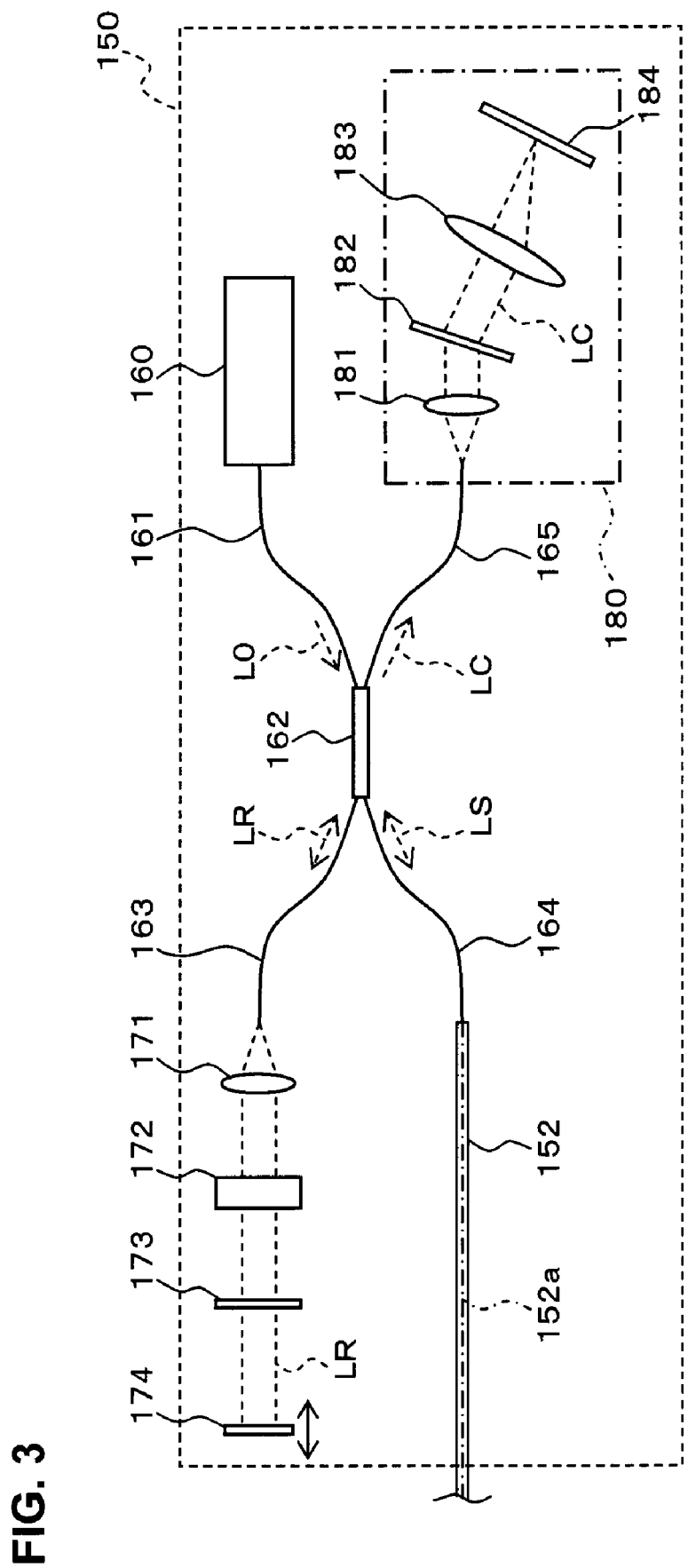
FIG. 3 is a schematic diagram representing one costitutional example of an OCT unit in a preferred embodiment of the fundus observation device related to the present invention.
Figure 4:
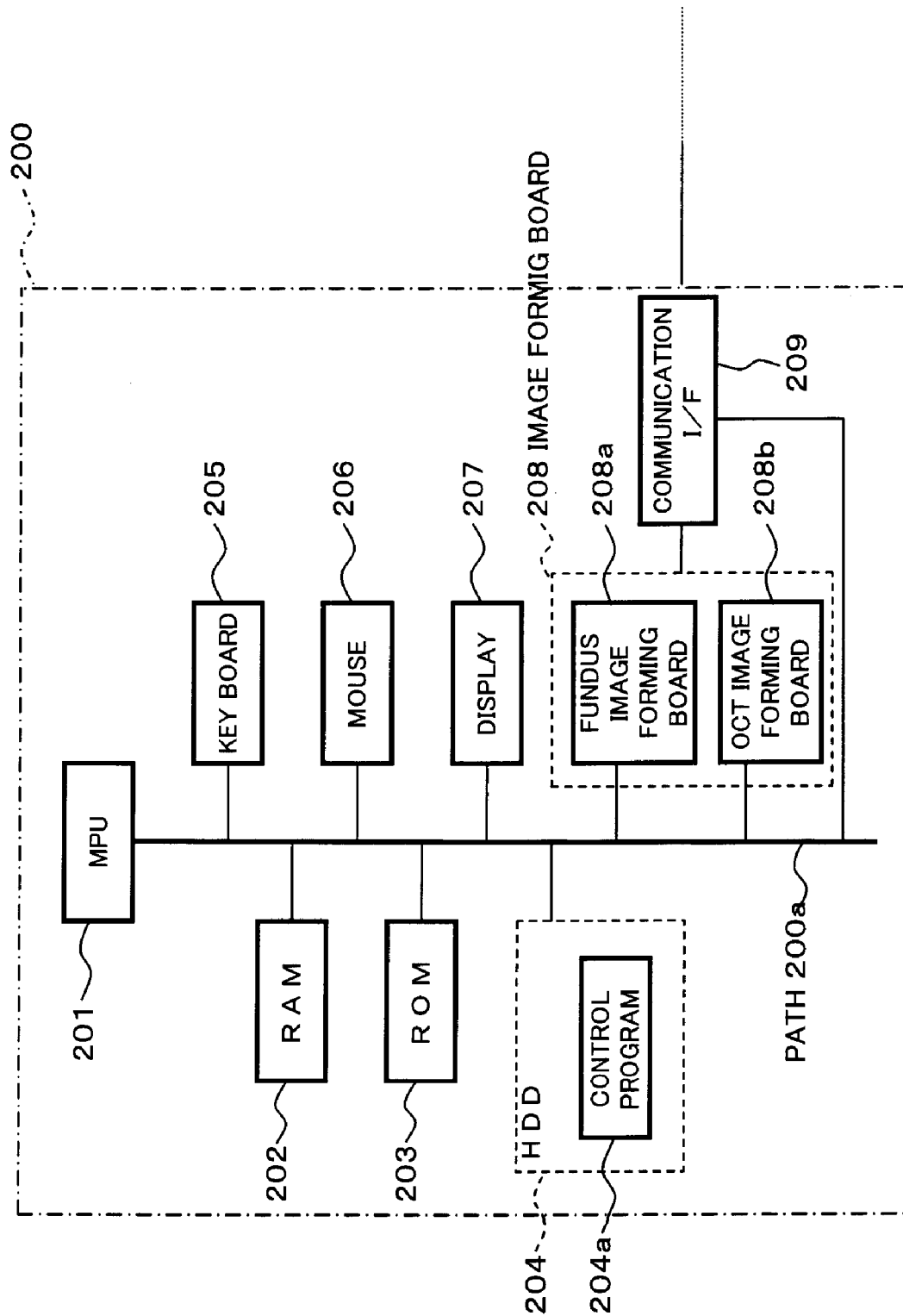
FIG. 4 is a schematic block diagram representing one example of hardware configurations of an arithmetic and control unit in an embodiment of the fundus observation device related to the present invention.
Figure 5:
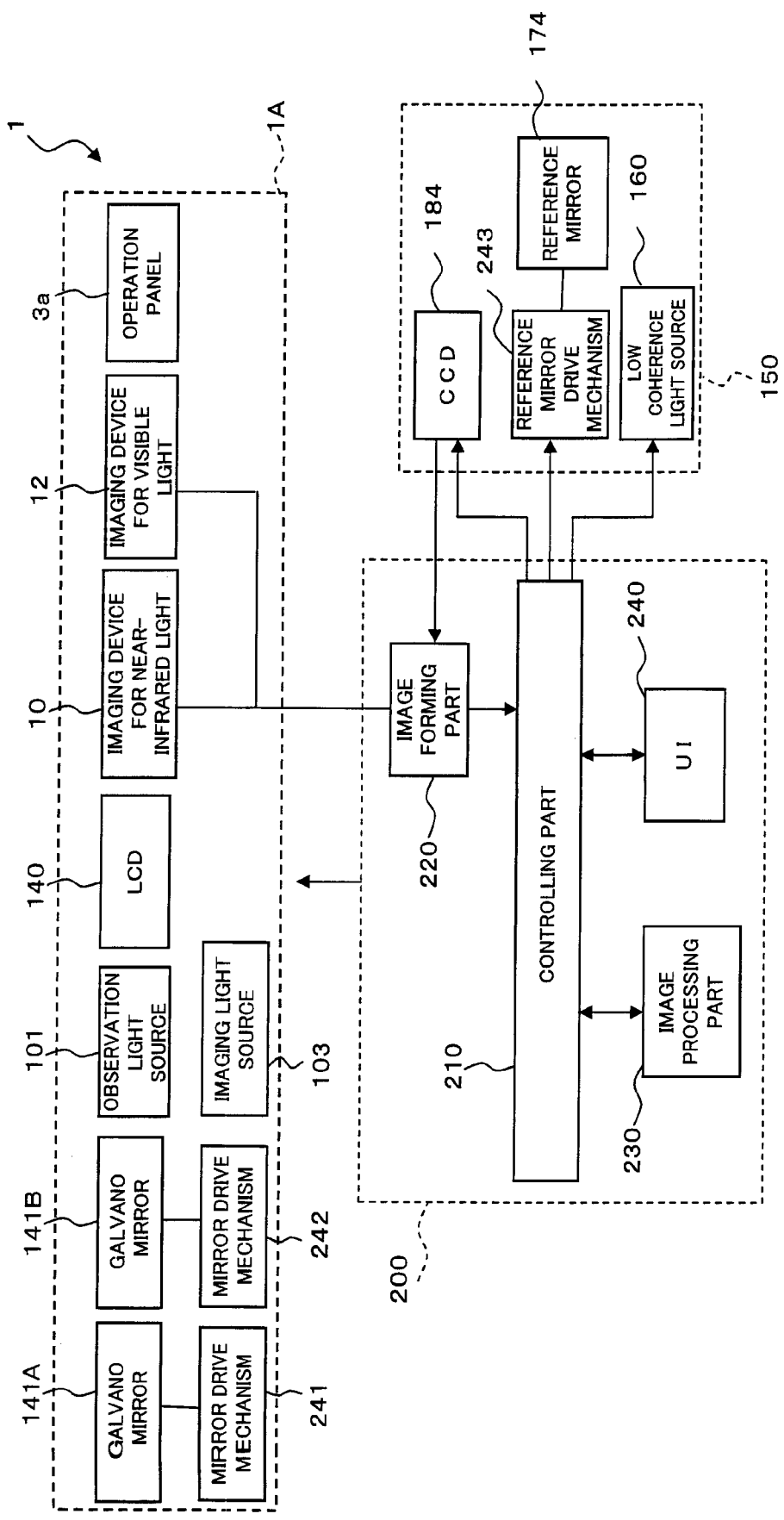
FIG. 5 is a schematic block diagram representing one costitutional example of a control system in a preferred embodiment of the fundus observation device related to the present invention.
Figure 6:
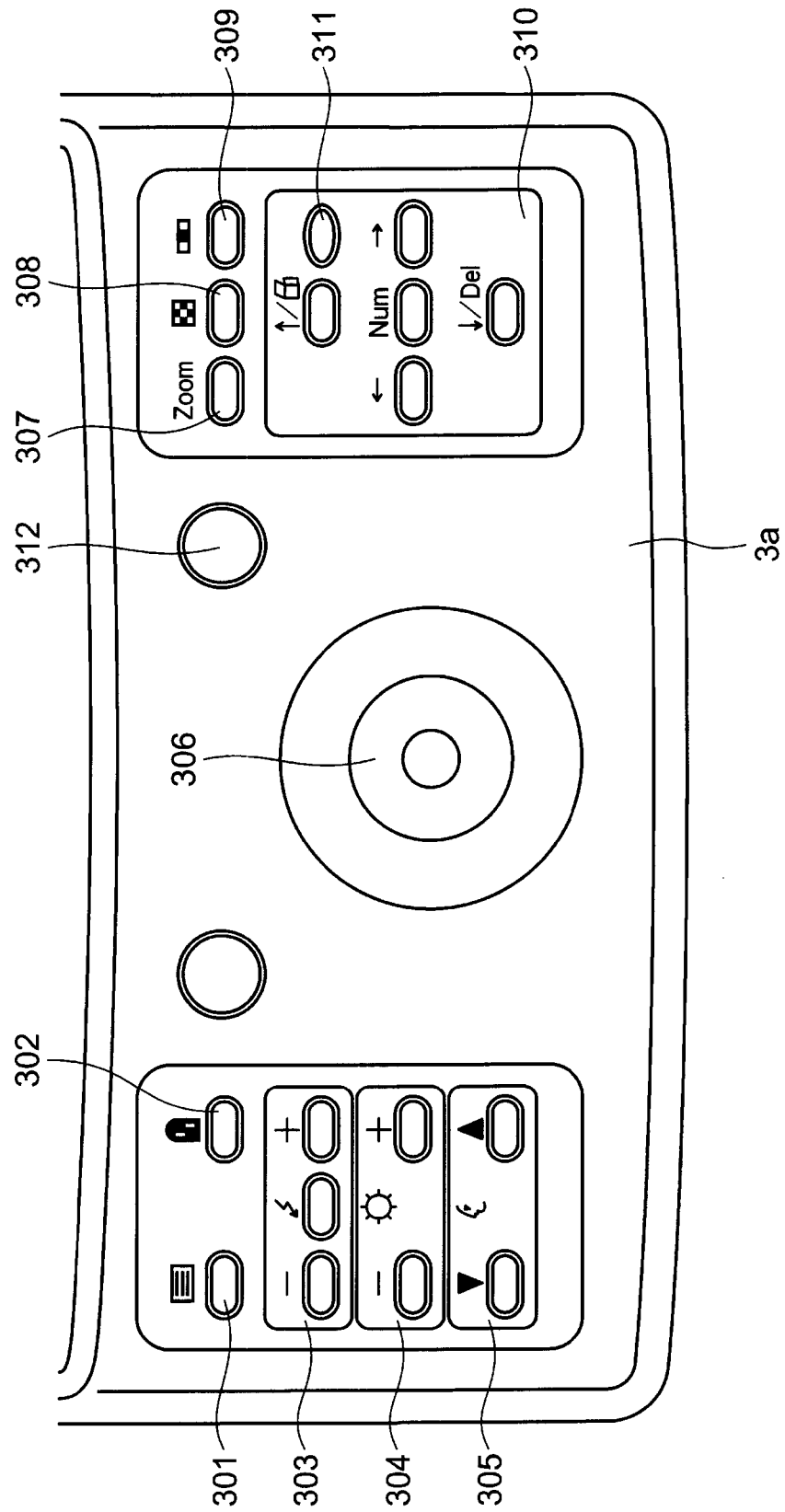
FIG. 6 is a schematic diagram showing an example of the apparent configuration of the operation panel in a preferred embodiment of the fundus observation device related to the present invention.
Figure 7:
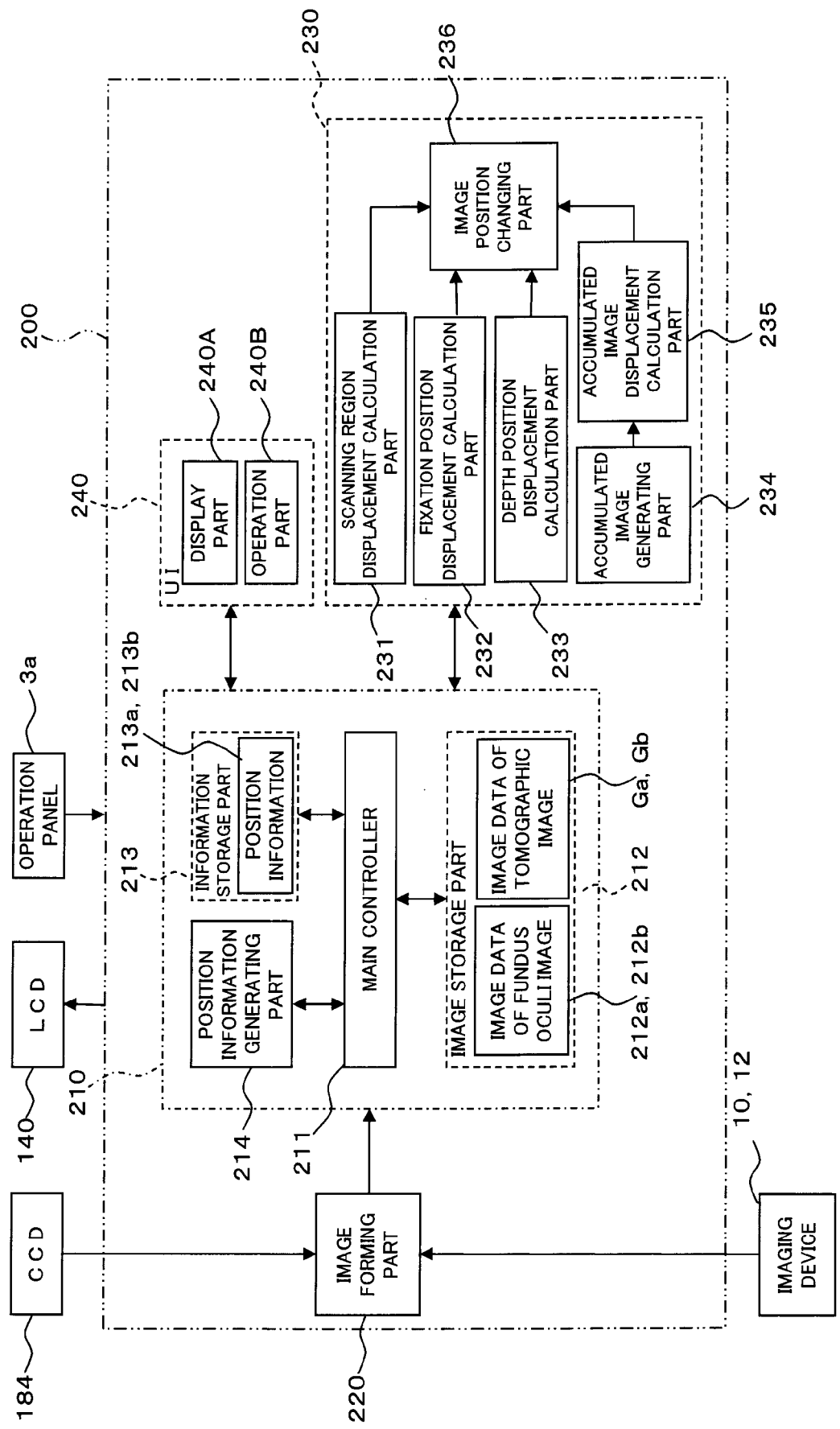
FIG. 7 is a drawing showing one example of configuration of the arithmetic and control unit in an preferred embodiment related to the present invention.

First, by referring to FIGS. 1 through 7, the constitution of the fundus observation device related to the present invention is described. FIG. 1 shows the entire constitution of the fundus observation device 1 related to the present invention. FIG. 2 shows a constitution of a scanning unit 141 in a fundus camera unit 1A. FIG. 3 shows a constitution of an OCT unit 150. FIG. 4 shows a hardware configuration of an arithmetic and control unit 200. FIG. 5 shows a configuration of a control system of the fundus observation device 1. FIG. 6 shows a constitution of an operation panel 3a provided on a fundus camera unit 1A. FIG. 7 shows a configuration of a control system of an arithmetic and control unit 200.

The Entire Configuration

As shown in FIG. 1, the fundus observation device 1 is comprised of a fundus camera unit 1A that functions as a fundus camera, an OCT unit 150 accommodating the optical system of an optical image measuring device (OCT device), and an arithmetic and control unit 200 that executes various arithmetic processes and control processes, etc.

To the OCT unit 150, one end of a connection line 152 is attached. To the other end of this connection line 152, a connector part 151 is attached. This connector part 151 is attached to a mounting part 8c shown in FIG. 13. Furthermore, a conductive optical fiber runs through the inside of the connection line 152. The OCT unit 150 and the fundus camera unit 1A are optically connected through the connection line 152. The constitution details of the OCT unit 150 are to be described later referring to FIG. 3.

Configuration of Fundus Camera Unit

A fundus camera unit 1A is a device for forming a 2-dimensional image of the surface of a fundus oculi of an eye based on optically captured data (data detected by imaging devices 10 and 12), and the fundus camera unit 1A has substantially the same appearance as the conventional fundus camera 1000 shown in FIG. 13. Furthermore, as in the conventional optical system shown in FIG. 14, the fundus camera unit 1A is provided with an illuminating optical system 100 to light a fundus oculi Ef of an eye E, and an imaging optical system 120 for guiding the fundus reflection light of the illumination light to an imaging device 10.

In addition, although the details are to be described later, an imaging device 10 in an imaging optical system 120 of the present embodiment is used for detecting the illumination light with a wavelength in the near-infrared region. Furthermore, in this imaging optical system 120, an imaging device 12 for detecting the illumination light with a wavelength in the visible region is provided separately. In addition, in this imaging optical system 120, it can guide the signal light from the OCT unit 150 to the fundus oculi Ef and the signal light through the fundus oculi Ef to the OCT unit 150.

Also, the illuminating optical system 100 is comprised as in conventional ones including: an observation light source 101, a condenser lens 102, an imaging light source 103, a condenser lens 104, an exciter filter 105 and 106, a ring transparent plate 107, a mirror 108, an LCD 109, an illumination diaphragm 110, a relay lens 111, an aperture mirror 112, and an objective lens 113.

The observation light source 101 emits the illumination light of a wavelength in the visible region included within about 400 nm to 700 nm. Furthermore, the imaging light source 103 emits the illumination light of a wavelength in the near-infrared region included within about 700 nm to 800 nm. The near-infrared light emitted from this imaging light source 103 is provided shorter than the wavelength of the light used by the OCT unit 150 (to be described later).

At the same time, the imaging optical system 120 comprises: an objective lens 113, an aperture mirror 112 (aperture part 112a thereof), an imaging diaphragm 121, a barrier filter 122 and 123, a variable magnifying lens 124, a relay lens 125, an imaging lens 126, a dichroic mirror 134, a field lens 128, a half mirror 135, a relay lens 131, a dichroic mirror 136, an imaging lens 133, an imaging device 10 (an image pick-up element 10a), a reflection mirror 137, an imaging lens 138, an imaging device 12 (an image pick-up element 12a), and a lens 139 and LCD (Liquid crystal Display) 140.

Figure 10:
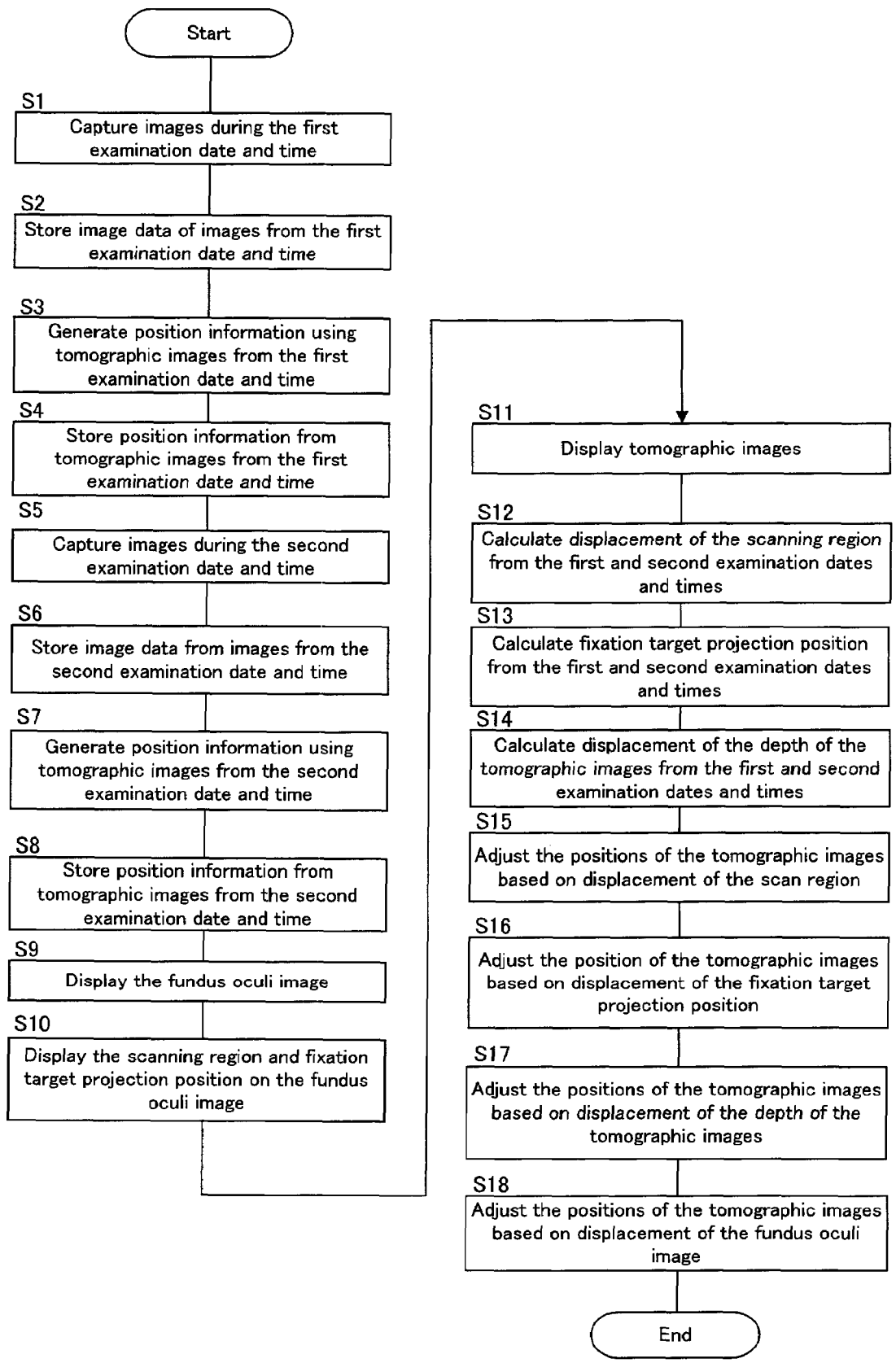
FIG. 10 is a flowchart that shows one example of the workings of a modification of the preferred embodiment of a fundus observation device related to the present invention.

The imaging optical system 120 related to the present embodiment is different from the conventional imaging optical system 120 shown in FIG. 10 in that the dichroic mirror 134, the half mirror 135, a dichroic mirror 136, the reflection mirror 137, the imaging lens 138, and the lens 139 and LCD 140 are provided.

The dichroic mirror 134 reflects the fundus reflection light of the illumination light (with a wavelength included within about 400 nm to 800 nm) from the illuminating optical system 100, and transmits the signal light LS (with a wavelength included within about 800 nm to 900 nm; to be described later) from the OCT unit 150.

Furthermore, the dichroic mirror 136 transmits the illumination light with a wavelength in the visible region from the illuminating optical system 100 (the visible light of a wavelength within about 400 nm to 700 nm emitted from the observation light source 101) and reflects the illumination lights having a wavelength in the near-infrared region (near-infrared light of a wavelength within about 400 nm to 700 nm emitted from the observation light source 101).

The LCD 140 shows an internal fixation target, etc. The light from this LCD 140 is reflected by the half mirror 135 after being converged by the lens 139, and is reflected by the dichroic mirror 136 through the field lens 128. Further, it enters the eye E passing through the imaging lens 126, the relay lens 125, the variable magnifying lens 124, the aperture mirror 112 (aperture part 112*a* thereof), the objective lens 113, etc. As a result, an internal fixation target, etc. is displayed in a fundus oculi Ef of an eye E.

The image pick up element 10*a* is the image pick up element of CCD and CMOS, etc. installed internally in an imaging device 10 such as a TV camera, and is particularly used for detecting light of a wavelength in the near-infrared region (that is, the imaging device 10 is the infrared TV camera for detecting near-infrared light). The imaging device 10 outputs the video signal as a result of detecting near-infrared light. A touch panel monitor 11 displays a 2-dimensional image (fundus image Ef') of the surface of the fundus oculi Ef based on this video signal. Also, this video signal is sent to the arithmetic and control unit 200, and the fundus oculi image is displayed on the display (to be described later). Furthermore, when the fundus oculi are being imaged by this imaging device 10, for example, the illumination light emitted from the imaging light source 103 of the illuminating optical system 100, having a wavelength in the near-infrared region, may be used.

Also, the image pick up element 12*a* is the image pick up element of CCD and CMOS, etc. installed internally in an imaging device 12 such as a TV camera, and is particularly used for detecting light of a wavelength in the visible region (that is, the imaging device 12 is the TV camera for detecting visible light). The imaging device 12 outputs the video signal as a result of detecting visible light. A touch panel monitor 11 displays a 2-dimensional image (fundus image Ef') of the surface of the fundus oculi Ef based on this video signal. Also, this video signal is sent to the arithmetic and control unit 200, and the fundus oculi image is displayed on the display (to be described later). Furthermore, when the fundus oculi are being imaged by this imaging device 12, for example, the illumination light emitted from the observation light source 101 of the illuminating optical system 100, having a wavelength in the visible region, may be used.

Furthermore, the imaging optical system 120 of the present embodiment is provided with a scanning unit 141 and a lens 142. The scanning unit 141 is equipped with a constitution to scan the light (signal light LS; to be described later) emitted from the OCT unit 150 on a fundus oculi Ef.

The lens 142 incidents the signal light LS from the OCT unit 150 in the form of parallel light flux onto the scanning unit 141. Furthermore, the lens 142 acts so as to converge the fundus reflection light of the signal light LS that has reached through the scanning unit 141.

In FIG. 2, one example of a concrete constitution of the scanning unit 141 is shown. The scanning unit 141 is comprised including Galvano mirrors 141A, 141B, and reflection mirrors 141C, 141D.

The Galvano mirrors 141A and 141B are to be rotatable centering around rotary shafts 141*a* and 141*b* respectively. The rotary shaft 141*a* and 141*b* are arranged perpendicular to each other. In FIG. 2, the rotary shaft 141*a* of the Galvano mirror 141A is arranged parallel to the paper face, while the rotary shaft 141*b* of the Galvano mirror 141B is arranged perpendicular to the paper face. That is, the Galvano mirror 141B is to be rotatable in the directions indicated by an arrow pointing in both directions in FIG. 2, while the Galvano mirror 141A is to be rotatable in the directions perpendicular to the arrow pointing in both directions. As a result, this pair of Galvano mirrors 141A and 141B act so that the reflecting direction of the signal light LS changes to a direction perpendicular to each other. Furthermore, the rotary movement of the Galvano mirror 141A and 141B respectively is driven by a drive mechanism (see FIG. 5) to be described later.

The signal light LS reflected by the Galvano mirrors 141A and 141B is to be reflected by reflection mirrors 141C and 141D, and is to advance in the same direction as having entered into the Galvano mirror 141A

As described previously, a conductive optical fiber 152*a* runs inside the connection line 152, and the end face 152*b* of the optical fiber 152*a* is arranged opposing the lens 142. The signal light LS emitted from this end face 152*b* advances while gradually expanding its beam diameter toward the lens 142 until being converged to a parallel light flux by this lens 142. On the contrary, the fundus reflection light of the signal light LS is converged toward the end face 152*b* by this lens 142.

Configuration of OCT Unit

Next, the configuration of an OCT unit 150 is described with reference to FIG. 3. The OCT unit 150 shown in the FIG. 3 is a device for forming a tomographic image of fundus oculi based on data captured by an optical scan (data detected by CCD 184 to be described below). The OCT unit 150 has a similar optical system to a conventional optical image measuring device. That is, the OCT unit 150 has an interferometer that splits the light emitted from a light source into a reference light and a signal light, and generates interference light by superposing the reference light having reached the reference object and the signal light having reached the object to be measured (fundus oculi Ef), and a device configured to output a signal as a result of detecting the interference light toward the arithmetic and control unit 200. The arithmetic and control unit 200 forms an image of the object to be measured (fundus oculi Ef) by analyzing this signal.

A low coherence light source 160 is composed of a broad band light source such as super luminescent diode (SLD) or a light emitting diode (LED), etc that emits low coherence light L0. This low coherence light L0, for instance, has a wave length in the near-infrared region and is supposed to be light having a time wise coherence length of approximately several tens of micro-meters. The low coherence light LO emitted from the low coherence light source 160 has a longer wavelength than the illumination light (wavelength: about 400 nm to 800 nm) of the fundus camera unit 1A, for example, a wavelength included within about 800 nm to 900 nm. This low coherence light source 160 corresponds to an example of the "light source" of the present invention.

The low coherence light L0 emitted from the low coherence light source 160 is guided to an optical coupler 162 through an optical fiber 161 composed of, e.g. a single mode fiber, or PM (Polarization maintaining) fiber, and then split into reference light LR and signal light LS.

Furthermore, the optical coupler 162 has both actions, i.e. a device for splitting lights (splitter), and a device for superposing lights (coupler); however, herein conventionally referred to as an "optical coupler".

The reference light LR generated by the optical coupler 162 is guided by an optical fiber 163 consisting of such as a single mode fiber, and emitted from the end face of the fiber. The emitted reference light LR is reflected by a reference mirror 174 (reference object) through a glass block 172 and a density filter 173 after having been converged into a parallel light flux by a collimator lens 171.

The reference light LR reflected by the reference mirror 174 is converged to the end face of the optical fiber 163 by the collimator lens 171 again through the density filter 173 and the glass block 172. The converged reference light LR is guided to the optical coupler 162 through the optical fiber 163.

Furthermore, the glass block 172 and the density filter 173 act as a delaying device for matching the optical path length (optical distance) between the reference light LR and the signal light LS, and as a device for matching the dispersion characteristics of reference light LR and the signal light LS.

Furthermore, the reference mirror 174 is provided to be movable in the propagating direction of the reference light LR. As a result, it ensures the light path length of the reference light LR according to the axial length, etc. of an eye E. Moreover, the reference mirror 174 is operated to move by a drive mechanism including a motor, etc.

Whereas, the signal light LS generated by the optical coupler 162 is guided to the end part of the connection line 152 by an optical fiber 164 consisting of such as a single mode fiber. A conductive optical fiber 152a runs inside the connection line 152. Herein, the optical fiber 164 and the optical fiber 152a may be composed of a single optical fiber, or may be jointly formed by connecting each end. In either case, it is sufficient as long as the optical fiber 164 and 152a are composed so as to be capable of transferring the signal light LS between the fundus camera unit 1A and the OCT unit 150.

The signal light LS is guided within the connection line 152 to the fundus camera unit 1A. Then, the signal light LS enters into the eye E through the lens 142, the scanning unit 141, the dichroic mirror 134 the imaging lens 126, the relay lens 125, the variable magnifying lens 124, the imaging diaphragm 121, the aperture part 112a of an aperture mirror 112, and the objective lens 113 (then, the barrier filter 122 and 123 are retracted from the optical path respectively).

The signal light LS that has entered into the eye E forms an image on a fundus oculi (retina) Ef and is then reflected. Then, the signal light LS is not only reflected on the surface of the fundus oculi Ef, but is also scattered at the refractive index boundary reaching the deep area of the fundus oculi Ef. As a result, the signal light LS reached the fundus Ef becomes a light containing the information reflecting the surface state of the fundus oculi Ef and the information reflecting the scattered state in the rear at the refractive index boundary of the deep area tissue. The light is simply referred as "fundus reflection light of the signal light LS.

The fundus reflection light of the signal light LS advances reversely on the above path and converges at the end face 152b of the optical fiber 152a, then enters into the OCT unit 150 through this optical fiber 152a, and returns to the optical coupler 162 through the optical fiber 164. The optical coupler 162 overlays this signal light LS on the reference light LR reflected at the reference mirror 174 to generate interference light LC. The generated interference light LC is guided into a spectrometer 180 through an optical fiber 165 consisting of such as a single mode fiber.

Herein, the "interference light generation part" relating to the present invention is comprised of an interferometer including at least an optical coupler 162, an optical fiber 163 and 164, and a reference mirror 174. Furthermore, although a Michelson type interferometer has been adopted in the present embodiment, for instance, a Mach Zender type, etc. or any optional type of interferometer may be adopted appropriately.

The spectrometer 180 is comprised of a collimator lens 181, a diffraction grating 182, an image forming lens 183, and a CCD (Charge Coupled Device) 184. The diffraction grating 182 in the present embodiment is a transmission type diffraction grating; however, needless to say, a reflection type diffraction grating may also be used. Furthermore, needless to say, in place of CCD 184, it is also possible to adopt other photo-detecting elements. This photo-detecting element is one example of the "second detecting part" relating to the present invention.

The interference light LC entered the spectrometer 180 is to be resolved into spectra by the diffraction grating 182 after having been converged into a parallel light flux by the collimator lens. The split interference light LC forms an image on the image pick up surface of the CCD 184 by the image forming lens 183. The CCD 184 receives this interference light LC that is to be converted to an electrical detection signal, and outputs this detection signal to the arithmetic and control unit 200.

Configuration of Arithmetic and Control Unit

Next, the configuration of the arithmetic and control unit 200 is described. This arithmetic and control unit 200 analyzes the detection signal input from the CCD 184 of the spectrometer 180 of the OCT unit 150, and performs a process of forming tomographic images of a fundus oculi Ef of an eye E. The analysis technique then is the same technique as the conventional Fourier domain OCT technique.

Also, the arithmetic and control unit 200 operates to form (image data of) a 2-dimensional image showing the state of the surface of a fundus oculi Ef (retina) based on the video signal output from the imaging device 10 and 12 of the fundus camera unit 1A.

Furthermore, the arithmetic and control unit 200 executes the control of each part of the fundus camera unit 1A and the control of each part of the OCT unit 150.

As for the control of the fundus camera unit 1A, to be controlled is, for example: the emission of illumination light by the observation light source 101 or the imaging light source 103; the insertion/retraction operation of the exciter filters 105, 106, or the barrier filters 122, 123 on the optical path; the display operation of the liquid crystal display 140; the shift of the illumination diaphragm 110 (controlling the diaphragm value); the diaphragm value of the imaging diaphragm 121; the shift of the variable magnifying lens 124 (controlling the magnification), etc.

Whereas, as for the control of the OCT unit 150, emission control of the low coherence light by a low coherence light source 160, control of accumulated time of the CCD 184, and movement control of reference mirror 174, etc. are to be performed.

The hardware configuration of the arithmetic and control unit 200 that acts as described above is explained referring to FIG. 4. The arithmetic and control unit 200 is provided with a hardware configuration that is the same as conventional computers. To be specific, the configuration includes: a microprocessor 201 (CPU, MPU, etc.), a RAM202, a ROM203, a hard disk drive (HDD) 204, a key board 205, a mouse 206, a display 207, an image forming board 208, and a communication interface (I/F) 209. Each part of these is connected through a bus 200a.

The microprocessor 201 executes operations characteristic to the present embodiment by loading a control program 204a that has been stored in the hard disk drive 204, on the RAM 202.

Furthermore, the microprocessor 201 executes control of each part of the device that has previously been described and various arithmetic processes, etc. Moreover, control of each part of the device that responds to an operation signal from the key board 205 or the mouse 206, control of display processes by the display 207, and control of transmitting/receiving processes of various types of data or control signals, etc. are executed by the communication interface 209.

The key board 205, the mouse 206 and the display 207 are used as a user interface of the fundus observation device 1. The key board 205 is used as a device for inputting letters or figures, etc. by typing. The mouse 206 is used as a device to perform various input operations with respect to the display screen of the display 207.

Furthermore, the display 207 as an arbitrary display device such as LCD (Liquid Crystal Display) or CRT (Cathode Ray Tube), etc. displays images of a fundus oculi Ef formed by the fundus observation device 1 and displays various operation screens or set up screens, etc.

Furthermore, the user interface of the fundus observation device 1 is not limited to such a configuration but may be configured by using any user interfaces equipped with a function to display various information and a function to input various information such as track ball, control lever, touch panel type LCD, control panel for ophthalmology examinations.

An image forming board 208 is a dedicated electronic circuit for operating to form (image data of) the image of the fundus oculi Ef of an eye E. In this image forming board 208, the fundus image forming board 208a and OCT image forming board 208b are installed. The fundus image forming board 208a is a dedicated electronic circuit for operating in order to form the image of the fundus oculi based on the video signal from the imaging device 10 or the imaging device 12 of the fundus camera unit 1A. Furthermore, the OCT image forming board 208b is a dedicated electronic circuit for operating in order to form image data of tomographic images of fundus oculi Ef based on the detecting signal from CCD 184 of the spectrometer 180 in the OCT unit 150. The image forming board 208 causes the processing speed for forming image data of fundus images and tomographic images to improve.

A communication interface 209 operates to send the control signal from a microprocessor 201 to the fundus camera unit 1A and OCT unit 150. Also, the communication interface 209 operates to receive the video signal from the imaging device 10 and 12 in the fundus camera unit 1A and the detecting signal from CCD 184 in the OCT unit 150, and it operates to input the signals to the image forming board 208. At this time, the communication interface 209 operates to input the video signal from the imaging device 10 and 12 to the fundus image forming board 208a, and it operates to input the detecting signal from CCD 184 to OCT image forming board 208b.

Moreover, when the arithmetic and control unit 200 is connected to a network such as LAN (Local Area Network) or Internet, etc., the communication interface 209 may be configured to be equipped with a network adopter such as LAN card, etc. or a communication equipment such as modem, etc. so as to be able to perform data communication through the network. In this case, a server accommodating the control program 204a may be installed, and at the same time, the arithmetic and control unit 200 may be configured as a client terminal of the server.

Control System Configuration

The configuration of the control system of the fundus observation device 1 having the configuration described above is explained referring to FIG. 5 and FIG. 7. FIG. 5 shows a part related to the operations or processes of the present embodiment that has been particularly selected from among constituents composing the fundus observation device 1. FIG. 6 shows a constitution of an operation panel 3a provided on a fundus camera unit 1A. FIG. 7 shows a detailed constitution of the arithmetic and control unit 200.

Controlling Part

The control system of the fundus observation device 1 is configured mainly having a controlling part 210 of the arithmetic and control unit 200. The controlling part 210 is comprised including: the microprocessor 201, the RAM202, the ROM203, the hard disk drive 204 (control program 204a), and the communication interface 209.

The controlling part 210 executes said controlling processes by the microprocessor 201 that is operated based on the control program 204a. In particular, it executes control of the mirror drive mechanism 241, 242 of the fundus camera unit 1A to independently work the Galvano mirrors 141A, 141B as well as control of the reference mirror drive mechanism 243 to move the reference mirror 174 toward the direction in which the reference light LR travels.

Furthermore, the controlling part 210 executes control for causing the display 207 of the user interface 240 to display two kinds of images produced by the fundus observation device 1: that is, a 2-dimensional image (fundus image Ef') of the surface of a fundus oculi Ef by the fundus camera unit 1A, and an tomographic image (sectional image, 3-dimensional image, etc.) of a fundus oculi Ef formed based on the detection signal obtained by the OCT unit 150. These images can be displayed on the display 207 both respectively and simultaneously. As to the details of constitution of the controlling part 210, it is described later according to FIG. 7.

Image Forming Part

An image forming part 220 is intended to operate the process forming the fundus image based on the video signal from the imaging device 10 and 12 of the fundus camera unit 1A and to operate the process forming image data of the tomographic images of fundus oculi Ef based on the detecting signal from CCD 184 in the OCT unit 150. This imaging forming part 220 comprises an imaging forming board 208. In addition, "image" may be identified with corresponding "image data" relating to the present invention.

An image forming part 220 is a configuration of one example of the "image forming part" relating to the present invention with a fundus camera unit 1A and OCT unit 150. Herein, each part of the fundus camera unit 1A for capturing a 2-dimensional image of the surface of the fundus oculi Ef and the image forming part 220 and explained as one example of the "first image forming part" relating to the present invention. In addition, each part of the fundus camera unit 1A for capturing a tomographic image of the fundus oculi Ef, the OCT unit 150, and the image forming part 220 and explained as one example of the "second image forming part" relating to the present invention.

Image Processing Part

The image processing part 230 is used for various image processes to image data of the images formed by the image forming part 220. For example, it operates to form image data of a 3-dimensional image of the fundus oculi Ef based on the tomographic images of the fundus oculi Ef corresponding to the detection signal from the OCT unit 150 and executes various corrections, such as brightness adjustment.

Herein, 3-dimensional data is image data made by assigning pixel values to each of a plurality of voxels arranged 3-dimensionally, referred to as volume data, voxel data, and so forth. When displaying an image based on volume data, the image processing part 230 operates to form image data of a pseudo 3-dimensional image seen from a particular viewing direction by applying a rendering process (such as volume rendering and MIP (Maximum Intensity Projection)) to this volume data. A display device such as a display device 207 will display such a pseudo 3-dimensional image based on the image data.

User Interface

The user interface (UI) 240, as shown in FIG. 7, comprises a display part 240A consisting of a display device such as a display 207, and an operation part 240B consisting of an operation device and an input device such as a keyboard 205 and mouse 206.

Operation Panel

The operation panel 3a of the fundus camera unit 1A is described below. This operation panel 3a is, as shown for example in FIG. 13, arranged on the platform 3 of the fundus camera unit 1A. The operation panel 3a in the present embodiment is different from the conventional configuration described above, which is provided with an operating part used to input an operation request for capturing a 2-dimensional image of the surface of the fundus oculi Ef and an operating part used for the input operation of capturing a tomographic image of the fundus oculi Ef (traditionally, only the former operating part). Consequently, the OCT can also be operated in the same manner as operation of a traditional fundus camera.

The operation panel 3a in the present embodiment is, as shown in FIG. 6, provided with a menu switch 301, a split switch 302, an imaging light amount switch 303, an observation light amount switch 304, a jaw holder switch 305, a photographing switch 306, a zoom switch 307, an image switching switch 308, a fixation target switching switch 309, a fixation target position adjusting switch 310, a fixation target size switching switch 311 and a mode switching knob 312.

The menu switch 301 is a switch operated to display a certain menu display for a user to select and specify various types of menus (such as a photographing menu for photographing a 2-dimensional image of the surface of the fundus oculi Ef and a tomographic image of the fundus oculi Ef, and a setting menu for inputting various types of settings). When this menu switch 301 is operated, the operation signal will be input to the controlling part 210. The controlling part 210 displays a menu screen on the touch panel monitor 11 or the display part 240A in response to the input of this operation signal. Incidentally, a controlling part (not shown) may be provided in the fundus camera unit 1A and this controlling part may cause the touch panel monitor 11 to display the menu screen.

The split switch 302 is a switch operated to switch the light on and off of the split bright line for focusing (e.g., see JP Patent laid-open No. H9-66031 or the like. Also referred to as split target, split mark and so on.). Incidentally, the configuration for projecting this split bright line onto an eye E to be examined (split bright line projection part) is housed, for example, in the fundus camera unit 1A (omitted in FIG. 1). When the split switch 302 is operated, the operation signal will be input to the controlling part 210 (or the above controlling part in the fundus camera unit 1A; hereinafter same as this). The controlling part 210 projects the split bright line onto the eye E to be examined by controlling the split bright line projection part in response to the input of this operation signal.

The imaging light amount switch 303 is a switch operated to adjust the emitted light amount of the imaging light source 103 (photographing light amount) depending on the state of the eye E to be examined (such as the degree of opacity of the lens). This imaging light amount switch 303 is provided with, for example, a photographing light amount increasing switch "+" for increasing the photographing light amount, a photographing light amount decreasing switch "−", and reset switch (button in the middle) for setting the photographing ling amount to a certain initial value (default value). When one of the imaging light amount switches 303 is operated, the operation signal will be input to the controlling part 210. The controlling part 210 adjust the photographing light amount by controlling the imaging light source 103 depending on the operation signal that was input.

The observation light amount switch 304 is a switch operated to adjust the emitted light amount (observation light amount) of the observation light source 101. The observation light amount switch 304 is provided with, for example, an observation light amount increasing switch "+" for increasing the observation light amount and an observation light amount decreasing switch "−" for decreasing the observation light amount. When one of the observation light amount switches 304 is operated, the operation signal will be input to the controlling part 210. The controlling part 210 adjusts the observation light amount by controlling the observation light source 101 depending on the operation signal that was input.

The jaw holder switch 305 is a switch to move the position of the jaw holder 6 shown in FIG. 13. This jaw holder switch 305 is provided with, for example, an upward movement switch (upward triangle) for moving the jaw holder 6 upward and a downward movement switch (downward triangle) for moving the jaw holder 6 downward. When one of the jaw holder switches 305 is operated, the operation signal will be input to the controlling part 210. The controlling part 210 moves the jaw holder 6 upward or downward by controlling the holder movement mechanism (not shown) depending on the operation signal that was input.

The photographing switch 306 is a switch used as a trigger switch for capturing a 2-dimensional image of the surface of the fundus oculi Ef or a tomographic image of the fundus oculi Ef. When the photographing switch 306 is operated with a menu to photograph a 2-dimensional image selected, the controlling part 210 that has received the operation signal will control the imaging light source 103, and the display part 240A or the touch panel monitor 11. The imaging light source 103 is controlled to emit the photographing illumination light. The display part 240A or the touch panel monitor 11 is controlled to display a 2-dimensional image of the surface of the fundus oculi Ef, based on the video signal output from the imaging device 10 that has detected the fundus reflection light.

On the other hand, when the photographing switch 306 is operated while a menu is selected to capture a tomographic image, the controlling part 210 that has received the operation signal will control the low coherence light source 160, galvanometer mirrors 141A and 141B, and display part 240A or the touch panel monitor 11. The low coherence light source 160 is controlled to emit the low coherence light LO. The galvanometer mirrors 141A and 141B are controlled to scan the signal light LS. The display part 240A or the touch panel monitor 11 is controlled to display a tomographic image of the fundus oculi Ef formed by the image forming part 220 (and image processing part 230), based on the detecting signal output from the CCD 184 that has detected the interference light LC.

The zoom switch 307 is a switch operated to change the angle of view (zoom magnification) for photographing of the fundus oculi Ef. Every time this zoom switch 307 is operated, for example, 45 degree and 22.5 degree of photographing angles of view will be set alternately. When this zoom switch 307 is operated, the controlling part 210 that has received the operation signal controls the variable magnifying lens driving mechanism (not shown). The variable magnifying lens driving mechanism moves the variable magnifying lens 124 in the optical axial direction for changing the photographing angle of view.

The image switching switch 308 is a switch operated to switch displaying images. When the image switching switch 308 is operated during a fundus oculi observation image (a 2-dimensional image of the surface of the fundus oculi Ef based on the video signal from the imaging device 12) is displayed on the display part 240A or the touch panel monitor 11, the controlling part 210 that has received the operation signal will control the display part 240A or the touch panel monitor 11. The display part 240A or the touch panel monitor 11 is controlled to display the tomographic image of the fundus oculi Ef. On the other hand, when the image switching switch 308 is operated during the display of a tomographic image of the fundus oculi on the display part 240A or the touch panel monitor 11, the controlling part 210 that has received the operation signal will control the display part 240A or the touch panel monitor 11. The display part 240A or the touch panel monitor 11 is controlled to display the fundus oculi observation image.

The fixation target switching switch 309 is a switch operated to switch the display position of the internal fixation target via the LCD 140 (i.e. the projection position of the internal fixation target on the fundus oculi Ef). By operating this fixation target switching switch 309, the display position of the internal fixation target can be switched, for example, among "fixation position to capture the image of the peripheral region of the center of the fundus oculi," "fixation position to capture the image of the peripheral region of macula lutea" and "fixation position to capture the image of the peripheral region of papilla," in a circulative fashion. The controlling part 210 controls the LCD 140 in response to the operation signal from the fixation target switching switch 309. The LCD 140 is then controlled to display the internal fixation target in the different positions on its display surface. Incidentally, the display positions of the internal fixation target corresponding with the above three fixation positions, for example, are preset based on clinical data or are set for each eye E to be examined (image of the fundus oculi Ef) in advance.

The fixation target position adjusting switch 310 is a switch operated to adjust the display position of the internal fixation target. This fixation target position adjusting switch 310 is provided with, for example, an upward movement switch for moving the display position of the internal fixation target upward, a downward movement switch for moving it downward, a leftward movement switch for moving it leftward, a rightward movement switch for moving it rightward, and a reset switch for moving it to a certain initial position (default position). The controlling part 210, when having received the operation signal from either of these switches, will control the LCD 140. The LCD 140 is controlled to move the display position of the internal fixation target.

The fixation target size switching switch 311 is a switch operated to change the size of the internal fixation target. When this fixation target size switching switch 311 is operated, the controlling part 210 that has received the operation signal will control the LCD 140. The LCD 140 is controlled to change the display size of the internal fixation target. The display size of the internal fixation target can be changed, for example, between "normal size" and "enlarged size," alternately. As a result, the size of the projection image of the fixation target projected onto the fundus oculi Ef is changed.

The mode switching knob 312 is a knob rotationally operated to select various types of photographing modes (such as a fundus oculi photographing mode to photograph a 2-dimensional image of the fundus oculi, a B scan mode to perform B scan of the signal light LS, and a 3-dimensional scan mode to have the signal light LS to be scanned 3-dimensionally). In addition, this mode switching knob 312 may be capable of selecting a replay mode to replay a captured 2-dimensional image or a tomographic image of the fundus oculi Ef. In addition, it may be capable of selecting a photographing mode to control so that the photographing of the fundus oculi Ef would be performed immediately after scanning the signal light LS. Control for performing each mode is executed by the controlling part 210.

The controlling feature of the scanning signal light LS by the controlling part 210 and the process feature to the detecting signal from the OCT unit 150 by the image forming part 220 and the image processing part 230 are respectively described below. Furthermore, an explanation regarding the process of the image forming part 220, etc., to the video signal from the fundus camera unit 1A is omitted because it is the same as the conventional process.

Regarding the Signal Light Scanning

Scanning of signal light LS is performed by changing the facing direction of the reflecting surfaces of the Galvano mirrors 141A and 141B of the scanning unit 141 in the fundus camera unit 1A. By controlling the mirror drive mechanisms 241 and 242 respectively, the controlling part 210 changes the facing direction of the reflecting surfaces of the Galvano mirror 141A and 141B, and scans the signal light LS on the fundus oculi Ef.

Once the facing direction of the reflecting surface of the Galvano mirror 141A is changed, the signal light LS is scanned in a horizontal direction (x-direction in FIG. 1) on the fundus oculi Ef. Whereas, once the facing direction of the reflecting surface of the Galvano mirror 141B is changed, the signal light LS is scanned in a vertical direction (y-direction in FIG. 1) on the fundus oculi Ef. Furthermore, by changing the facing direction of the reflecting surfaces of both Galvano mirrors 141A and 141B simultaneously, the signal light LS may be scanned in the composed direction of x-direction and y-direction. That is, by controlling these two Galvano mirrors 141A and 141B, the signal light LS may be scanned in an arbitrary direction on the xy plane.

Figure 8A:
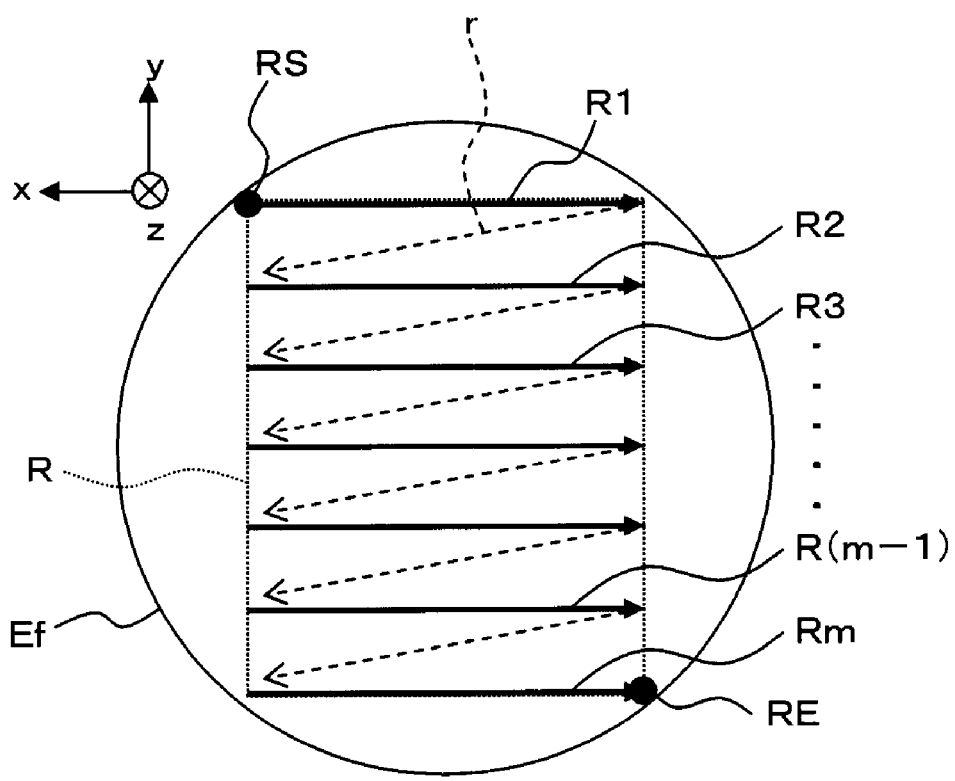
FIG. 8A represents one example of the scanning features of signal light when a fundus oculi is seen from the incident side of the signal light with respect to an eye. In addition.
Figure 8B:
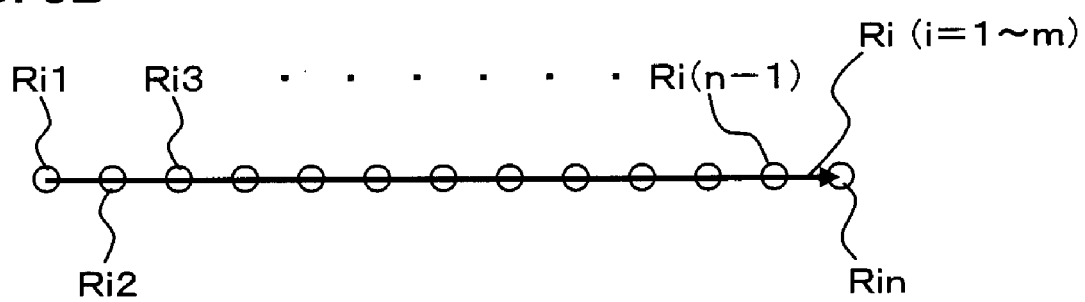
FIG. 8B represents one example of arrangement features of scanning points of each scanning line.

FIG. 8 represents one example of scanning features of signal light LS for forming images of a fundus oculi Ef. FIG. 8A represents one example of scanning features of the signal light LS, when the signal light LS sees the fundus oculi Ef from an incident direction onto the eye E (that is, +direction of z is seen from −direction of z in FIG. 1). Furthermore, FIG. 8B represents one example of arrangement features of scanning points (positions at which image measurement is carried out) on each scanning line on the fundus oculi Ef.

As shown in FIG. 8A, the signal light LS is scanned within a rectangular shaped scanning region R that has been preset. Within this scanning region R, plural (m number of) scanning lines R1 through Rm have been set in the x-direction. When the signal light LS is scanned along each scanning line Ri (i=1 through m), detection signals of interference light LC are to be generated.

Herein, the direction of each scanning line Ri is referred as the "main scanning direction" and the orthogonally crossing direction is referred as the "sub-scanning direction". Therefore, the scanning of the signal light LS in a main scanning direction is performed by changing the facing direction of the reflecting surface of the Galvano mirror 141A, and the scanning in a sub-scanning direction is performed by changing the facing direction of the reflecting surface of the Galvano mirror 141B.

On each scanning line Ri, as shown in FIG. 8B, plural (n number of) of scanning points Ri1 through Rin have been preset.

In order to execute the scanning shown in FIG. 8, the controlling part 210 controls the Galvano mirrors 141A and 141B to set the incident target of the signal light LS with respect to a fundus oculi Ef at a scan start position RS (scanning point R11) on the first scanning line R1. Subsequently, the controlling part 210 controls the low coherence light source 160 to flush the low coherence light L0 for emitting the signal light LS to the scan start position RS. The CCD 184 receives the interference light LC based on the fundus reflection light of this signal light LS at the scan start position RS, and outputs the detection signal to the controlling part 210.

Next, by controlling the Galvano mirror 141A the controlling part 210 scans the signal light LS in a main scanning direction and sets the incident target at a scanning point R12, triggering a flush emission of the low coherence light L0 for making the signal light LS incident onto the scanning point R12. The CCD 184 receives the interference light LC based on the fundus reflection light of this signal light LS at the scanning point R12, and then outputs the detection signal to the controlling part 210.

Likewise, the controlling part 210 obtains detection signals output from the CCD 184 responding to the interference light LC with respect to each scanning point, by flush emitting the low coherence light L0 at each scanning point while shifting the incident target of the signal light LS from scanning point R13, R14, - - -, R1(n−1), R1n in order.

Once the measurement at the last scanning point R1n of the first scanning line R1 is finished, the controlling part 210 controls the Galvano mirrors 141A and 141B simultaneously and shifts the incident target of the signal light LS to the first scanning point R21 of the second scanning line R2 following a line switching scan r. Then, by conducting the previously described measurement with regard to each scanning point R2j (j=1 through n) of this second scanning line R2, a detection signal corresponding to each scanning point R2j is obtained.

Likewise, by conducting a measurement with respect to the third scanning line R3, - - -, the m−1th scanning line R(m−1), the mth scanning line Rm respectively to obtain the detection signal corresponding to each scanning point. Furthermore, the symbol RE on a scanning line Rm is a scan end position in accordance with a scanning point Rmn.

As a result, the controlling part 210 obtains m×n number of detection signals corresponding to m×n number of scanning points Rij (i=1 through m, j=1 through n) within the scanning region R. Hereinafter, a detection signal corresponding to the scanning point Rij may be represented as Dij.

Such interlocking control of such shifting of scanning points and the emission of the low coherence light L0 may be realized by synchronizing, for instance, the transmitting timing of control signals with respect to the mirror drive mechanisms 241, 242 and the transmitting timing of control signals (output request signal) with respect to the low coherence light source 160.

As described, when each Galvano mirror 141A and 141B is being operated, the controlling part 210 stores the position of each scanning line Ri or the position of each scanning point Rij (coordinates on the xy coordinate system) as information indicating the content of the operation. This stored content (scan positional information) is used in an image forming process as was conducted conventionally.

Regarding Image Processing

Next, one example of the process relating to OCT images is described of the image forming part 220 and the image processing part 230.

The image forming part 220 executes the formation process of tomographic images of a fundus oculi Ef along each scanning line Ri (main scanning direction). The image processing part 230 executes the formation process of a 3-dimensional image of the fundus oculi Ef based on these tomographic images formed by the image forming part 220.

The formation process of a tomographic image by the image forming part 220, as was conventionally done, includes a 2-step arithmetic process. In the first step of the arithmetic process, based on a detection signal Dij corresponding to each scanning point Rij, an image in the depth-wise direction (z-direction in FIG. 1) of a fundus oculi Ef at the scanning point Rij is formed.

Figure 9:
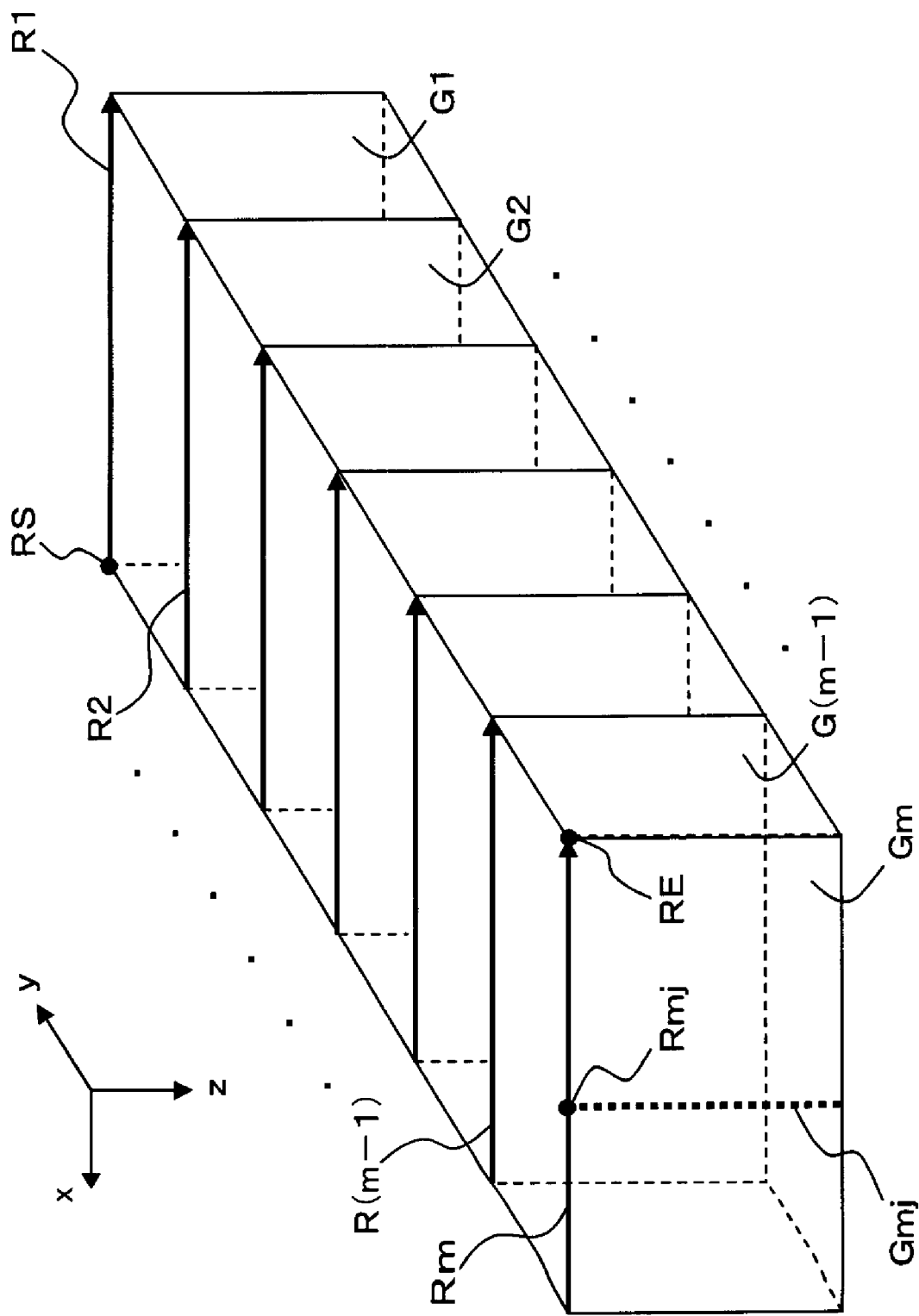
FIG. 9 is a schematic diagram representing one example of the scanning features of signal light and tomographic image features formed along each scanning line in a preferred embodiment of the fundus observation device related to the present invention.

FIG. 9 represents a feature of (a group of) tomographic images formed by the image forming part 220. In the second step of the arithmetic process, with regard to each scanning line Ri, based on the images in the depth-wise direction at the n number of scanning points Ri1 through Rin thereon, a tomographic image Gi of a fundus oculi Ef along this scanning line Ri is formed. Then, the image forming part 220 determines the arrangement and the distance of each scanning point Ri1 through Rin while referring to the positional information (said scan positional information) of each scanning point Ri1 through Rin, and forms a tomographic image Gi along this scanning line Ri. Due to the above process, m number of tomographic images (a group of tomographic images) G1 through Gm at different positions of the sub-scanning direction (y-direction) are obtained. Each of these tomographic images corresponds to the image data Ga in FIG. 7 (to be described later).

Next, the formation process of a 3-dimensional image of a fundus oculi Ef by the image processing part 230 is explained. A 3-dimensional image of a fundus oculi Ef is formed based on the m number of tomographic images obtained by the above arithmetic process. The image processing part 230 forms a 3-dimensional image of the fundus oculi Ef by performing a known interpolating process to interpolate an image between the adjacent tomographic images Gi and G(i+1).

Then, the image processing part 230 determines the arrangement and the distance of each scanning line Ri while referring to the positional information of each scanning line Ri to form this 3-dimensional image. For this 3-dimensional image, a 3-dimensional coordinate system (x,y,z) is set up, based on the positional information (said scan positional information) of each scanning point Rij and the z coordinate in the images of the depth-wise direction.

Furthermore, based on this 3-dimensional image, the image processing part 230 is capable of forming a tomographic image of the fundus oculi Ef at a cross-section in an arbitrary direction other than the main scanning direction (x-direction). Once the cross-section is designated, the image processing part 230 determines the position of each scanning point (and/or an image in the depth-wise direction that has been interpolated) on this designated cross-section, and extracts an image (and/or image in the depth-wise direction that has been interpolated) in the depth-wise direction at each determined position to form a tomographic image of the fundus oculi Ef at the designated cross-section by arranging plural extracted images in the depth-wise direction.

Furthermore, the image Gmj in FIG. 9 represents an image in the depth-wise direction (z-direction) at the scanning point Rmj on the scanning line Rm. Likewise, an image in the depth-wise direction at each scanning point Rij on the scanning line Ri formed by the arithmetic process of said first step may be represented as "image Gij."

Detailed Configuration of the Arithmetic and Control Unit

Detailed configuration of the arithmetic and control unit 200 is described with reference to FIG. 7. Herein, configuration of the controlling part 210 and the image processing part 230 of the arithmetic and control unit 200 is described.

The controlling part 210 is provided with a main controller 211, an image storage part 212, an information storage part 213 and a position information generating part 214.

In addition, the image processing part 230 is provided with a scanning region displacement calculation part 231, a fixation position displacement calculation part 232, a depth position displacement calculation part 233, an accumulated image generating part 234, an accumulated image displacement calculation part 235 and an image position changing part 236. This image processing part 230 is an example of the "image processing part" relating to the present invention.

Main Controller

The main controller 211 comprises a microprocessor 201 or the like and controls each part of the fundus observation device 1 (previously described).

Image Storage Part

The image storage part 212 stores image data of a 2-dimensional image of the surface of the fundus oculi Ef (fundus oculi image) formed by the image forming part 220 (e.g., image data indicated by symbols 212a and 212b) or image data of a tomographic image (e.g., image data indicated by symbols Ga, and Gb). A memory processing of image data to the image storage part 212 and a read processing of image data from the image storage part 212 are performed by the main controller 211. The image storage part 212 includes a memory device such as a hard disk drive 204.

Incidentally, the image data 212a of a fundus oculi image and the image data Ga or a tomographic image shall have been captured almost at the same time. In addition, the image data 212b of a fundus oculi image and the image dada Gb of a tomographic image shall have been captured almost at the same time. Herein, "captured almost at the same time (generally simultaneously)" shall mean that the both image data have been captured at most with little time difference such as the case where the both image data have been captured at the same time, the case where one image data has been captured immediately after the other image data has been captured, and the case where the both image data have been captured in a series of examination processes. On the contrary, for the image data 212a or the like and the image data 212b or the like, one has been captured after an appreciable time interval of capturing the other image data, for example, the examination date and time when they have been captured are different.

Information Storage Part

The information storage part 213 stores position information (e.g., information indicated by symbols 213a and 213b). This position information is information indicating, for a 2-dimensional image of the surface of a fundus oculi Ef (fundus oculi image) and the tomographic image, the position of this tomographic image in this fundus oculi image. The position information is generated by a position information generating part 214 (the generating method thereof will be described later).

This position information is described in more detail. A 2-dimensional X-Y coordinate system is predefined on an imaging area of an image pick-up element 10a of the imaging device 10 (not shown). The 2-dimensional coordinates being based on this X-Y coordinate system are set on the fundus oculi image photographed by this imaging device 10. This X-Y coordinate system defines a plane parallel to a plane made by x coordinates and y coordinates of the x-y-z coordinate system shown in FIG. 1. Herein, scales (lengths of the unit distance) of the two coordinate systems may be either equal or different. In addition, the directions of the coordinate axes of the two coordinate systems may either coincide with each other or not.

Generally, in the case where the scales and the directions of the coordinate axes of the two coordinate systems are both different, the direction of the coordinate axes can be coincident with each other by parallel transfer and rotational transfer, and the scales can be coincident with each other by enlarging/contracting the length of the unit distance of the coordinate axes (in other words, an unique coordinate transformation can be performed.).

In addition, as shown in FIG. 1, in the direction perpendicular to the x-y plane (X-Y plane), z coordinate (Z coordinate; not shown) whose positive direction is the depth direction of the fundus oculi Ef is defined. Also, for z coordinate and Z coordinate, their scales may be either equal or different. Hereinafter, X-Y-Z coordinate system and x-y-z coordinate system shall be coincident with each other in the directions of each corresponding coordinate axis and the scale of each coordinate axis shall be equal.

Each position information stored in the information storage part 213 includes, for example, at least any of the following information, that is, scanning region information, fixation position information, or depth information. Incidentally, the position information related to the present invention does not always include one of this information; any information indicating the position of a tomographic image in a fundus oculi image may be enough.

The scanning region information is information indicating the region in which the signal light LS was scanned upon capturing a tomographic image (scanning region) in x-y coordinate system. For the scanning region of the signal light LS, one example thereof is shown in FIG. 8. In the scanning feature shown in FIG. 8, the signal light LS is scanned in the main scanning direction (direction parallel to x axis) and sub scanning direction (direction parallel to y axis) as described before to form a rectangle-shaped scanning region R. The scanning region information corresponding with this scanning region R can be represented by the range of the main scanning direction and the range of the sub scanning direction, for example, like $(x1 \leq x \leq x2, y1 \leq y \leq y2)$.

Incidentally, the shape of the scanning region of the signal light LS is not limited to rectangular, for example, in the case of scanning the signal light LS concentrically or spirally, a circular scanning region will be formed. The scanning region information of this case can be represented by, for example, the coordinates of the center of the circular scanning region (x0, y0) and the radius r.

The fixation position information is information indicating the projection position of the inner fixation position onto the fundus oculi Ef upon capturing a tomographic image in x-y coordinate system. This fixation position information can be represented by, for example, the coordinate values (xf, yf) of the center position of the internal fixation target projected onto the fundus oculi Ef.

Incidentally, the fixation position information is not limited to the information directly indicating the actual projection position of the internal fixation target projected onto the fundus oculi Ef by x-y coordinate system. For example, it is possible to use, for example, the information obtained by transforming the display position of the internal fixation target on the LCD 140 (coordinate values represented by the 2-dimensional coordinate system defined on the surface of the LCD 140) as fixation position information. Herein, since the internal fixation target is displayed on the LCD 140 and projected onto the fundus oculi Ef by the imaging optical system 120, the calculations for the projection position on the fundus oculi Ef can be performed based on the display position on the LCD 140, the optical data of the imaging optical system 120, the alignment position of the z direction of the fundus oculi Ef and so on.

The depth information is information indicating the position of a tomographic image of the fundus oculi Ef depth-wise (z coordinate values), in other words, information indicating the depth-wise position of the fundus oculi image to the surface of the fundus oculi Ef (that is a subject to be photographed of the fundus oculi image).

The fundus oculi Ef has retina, choroidea and sclera. As depth information, the position in the z direction of an image in the tomographic image corresponding to a particular layer included in any of these membranes can be used. For example, it is possible to employ the position in the z direction of the image corresponding to the retinal pigment epithelium layer (or the boundary between retinal pigment epithelium and choroidea) in a tomographic image as depth information. Herein, the retinal pigment epithelium layer is a layer well reflecting the signal light LS and is depicted relatively clearly in a tomographic image, so can be preferably used as criteria of depth information.

Incidentally, in a tomographic image including papilla, for example, the position in the z direction (z coordinate values) in the image corresponding to the bottom of a crater of papilla in a tomographic image can be used as depth information.

Position Information Generating Part

The position information generating part 214 performs the process for generating the above-mentioned position information, and is one example of the "position information generating part" relating to the present invention. Hereinafter, the process for generating scanning region information, the process for generating fixation position information, and the process for generating depth information are respectively described.

First, the process for generating scanning region information is described. The scanning region of the signal light LS is specified by a user operating the operation part 240B or the like prior to capturing a tomographic image of the fundus oculi Ef. This operation is performed by displaying an observation image of the fundus oculi Ef on the display part 240A and performing a drag and drop operation with a mouse so as to surround the desired region on the observation image. For example, when a drag and drop operation is performed, a rectangle-shaped scanning region will be set whose diagonal line connects the position where the drag operation of the mouse starts and the position where the drop operation is performed.

The position information generating part 214 generates scanning region information when a fundus oculi image (photographing image) and a tomographic image of the fundus oculi Ef are captured at almost the same time based on the scanning region specified on the observation image of the fundus oculi Ef. At this time, the fixation position of an eye E when the observation image is displayed and the fixation position when a fundus oculi image and a tomographic image are captured shall be the same.

One specific example of the generating process of scanning region information when the scanning region is specified with the drag and drop operation of a mouse is described. When the scanning region has been specified, x coordinate value and y coordinate value of the drag starting position and x coordinate value and y coordinate value of the drop position are input to the controlling part 210 from the user interface 240, and sent to the position information generating part 214. Provided that the coordinates of the drag starting position are (x1, y1) and the coordinates of the drop position are (x2, y2), the position information generating part 214 generates scanning region information consisting of the region (x1≦x≦x2, y1≦y≦y2) on the fundus oculi image.

Next, the process for generating fixation position information is described. The fixation position of the eye E to be examined is specified by a user operating the fixation target switching switch 309, the fixation target position adjusting switch 310, or the fixation target size switching switch 311 of the operation panel 3a and so on prior to capturing a tomographic image of the fundus oculi Ef.

When the fixation position of the eye E to be examined is specified by the internal fixation target, the position information generating part 214 obtains, for example, the coordinate values (xf, yf) of the center position of the internal fixation target projected onto the fundus oculi Ef, and defines the coordinate values (xf, yf) as the fixation position information. At this time, it may be configured to determine the intended coordinate value by analyzing the observation image (before photographing) and the fundus oculi image (after photographing) onto which the internal fixation target has been projected, and it may also be configured to perform calculations for the intended coordinate value based on the displaying position of the internal fixation target displayed on the LCD 140.

Next, the process for generating depth information is described. When a tomographic image of the fundus oculi Ef has been captured, the image data of the tomographic image will be input to the position information generating part 214. The position information generating part 214 analyzes this image data, extracts for example a part corresponding to the retinal pigment epithelium layer, calculates the z coordinate value of this extracted part in this tomographic image, and defines this z coordinate value as the intended depth information.

Herein, it is also possible to analyze data provided for forming a tomographic image, for example, the data indicating the detection intensity distribution of the interference light LC at each depth position, instead of analyzing image data, determine z coordinate of the depth position where the detected intensity is the peak, and define it as the depth information.

The position information generated as above will be associated with the image data of the corresponding fundus oculi image and the image data of the corresponding tomographic image, and will be stored into the information storage part 213.

Scan Region Displacement Calculation Part

The scanning region displacement calculation part 231 performs calculations based on the coordinates of the scanning region of the signal light LS shown in each of two scanning region information, for displacement of those two coordinates (in the x-y direction). Provided that the coordinates shown in the scanning region information corresponding with the scanning region R upon capturing the first tomographic image are ($x1 \leq x \leq x2$, $y1 \leq y \leq y2$) and the coordinates shown in the scanning region information corresponding with the scanning region R' (not shown) upon capturing the second tomographic image are ($x1' \leq x \leq x2'$, $y1' \leq y \leq y2'$), the scanning region displacement calculation part 231 performs calculations for, for example, the displacements in the x direction, $\Delta x(min)=x1-x1'$ and $\Delta x(max)=x2-x2'$, and the displacements in the y direction, $\Delta y(min)=y1-y1'$ and $\Delta y(max)=y2-y2'$, respectively.

Herein, when the lengths of the scanning region R and R' in the x direction are equal (that is, when $x2-x1=x2'-x1'$), it is sufficient only to calculate $\Delta x=x1-x1'$ (or $x2-x2'$) as displacement in the x direction. Similarly, when the lengths of the scanning region R and R' of the y direction are equal (that is, when $y2-y1=y2'-y1'$), it is sufficient only to calculate $\Delta y=y1-y1'$ (or $y2-y2'$) as displacement in the y direction. The scanning region displacement calculation part 231 is an example of the "displacement calculating part" relating to the present invention.

Fixation Position Displacement Calculation Part

The fixation position displacement calculation part 232 performs calculations, based on the coordinates of the projection position of the inter fixation target onto the fundus oculi Ef shown in each of two fixation position information, for the displacements (in the x-y direction) of those two coordinates. Provided that the coordinates of the projection position of the inter fixation target shown in the fixation position information corresponding with the first tomographic image are (xf, yf) and the coordinates of the projection position of the inter fixation target corresponding with the second tomographic image are (xf', yf'), the fixation position displacement calculation part 232 performs calculations for the displacement of the x direction, $\Delta xf=xf-xf'$ and the displacement of the y-direction $\Delta yf=yf-yf'$ of those two coordinates, respectively. The fixation position displacement calculation part 232 is an example of the "displacement calculating part" relating to the present invention.

Depth Position Displacement Calculation Part

The depth position displacement calculation part 233 performs calculations for, based on the coordinates of the depth position shown in each of two depth information, displacement (depth-wise, i.e. in the z direction) of those two coordinates. Provided that the coordinate shown in the depth information corresponding with the first tomographic image is z and the coordinate shown in the depth information corresponding with the second tomographic image is z', the depth position displacement calculation part 233 performs calculation for the displacement of these two coordinates $\Delta z=z-z'$.

Accumulated Image Generating Part

The accumulated image generating part 234 accumulates each of the tomographic images formed by the image forming part 220 depth-wise and generates a 1-dimensional image (accumulated image). That is, the accumulated image generating part 234 accumulates the each depth-wise image Gij comprising a tomographic image Gi depth-wise (in z direction) and forms point-like images. Each point-like image shows accumulated luminance at the position of the depth-wise image Gij. Herein, "accumulating depth-wise" means the calculation processing for summing (projecting) luminance value at each depth position of the depth-wise image.

By performing such a processing for each tomographic image obtained by a series of scan of the signal light LS, an image indicating the surface figure of the fundus oculi Ef in this scanning region as well as a fundus oculi image (2-dimensional image of the surface) are obtained. Incidentally, accumulated images are described in detail in Japanese Patent Application No. 2005-337628 by the present inventors. The accumulated image generating part 234 is an example of the "accumulated image generating part" relating to the present invention.

Accumulated Image Displacement Calculation Part

The accumulated image displacement calculation part 235 performs calculations for, based on two accumulated images based on the first and second (group of) tomographic image(s), the displacement of those accumulated images in the x-y direction. An accumulated image is formed in the range of the same x-y coordinates as the scanning region of the signal light LS when capturing the tomographic images. The accumulated image displacement calculation part 235 performs calculations for the displacement of two accumulated images based on the coordinates of the scanning region corresponding with each accumulated image (e.g., obtained with reference to the scanning region information) in the same fashion as the scanning region displacement calculation part 231.

As another example of the process for performing calculations for the displacement of two accumulated images, it is also possible to perform calculations for the displacement so that correlation between two accumulated images is the highest. In addition, it is also possible to be configured to obtain the displacement of the two accumulated images by extracting characteristic points from the two accumulated images respectively and performing calculations for the displacement of each of the characteristic points. The accumulated image displacement calculation part 235 is one example of the "accumulated image displacement calculating part" relating to the present invention.

Image Position Changing Part

The image position changing part 236 adjusts the position of two (groups of) tomographic images by changing the position of the (groups of) tomographic images based on the information of the displacements input from the scanning region displacement calculation part 231, the fixation position displacement calculation part 232, the depth position displacement calculation part 233 and the accumulated image displacement calculation part 235. The image position changing part 236 is one example of the "image position changing part" relating to the present invention.

Hereinafter, the position adjustment process of images based on the displacement input from the scanning region displacement calculation part 231, the position adjustment process of images based on the displacement input from the fixation position displacement calculation part 232, the position adjustment process of images based on the displacement input from the depth position displacement calculation part 233, and the position adjustment process of images based on the displacement input from the accumulated image displacement calculation part 235 are respectively described. In addition, the detailed position adjustment of (groups of) tomographic images by the image position changing part 236 is also described.

First, the position adjustment process of images based on the displacement input from the scanning region displacement calculation part 231 is described. The image position changing part 236 adjusts the position of two (groups of) tomographic images in the x direction and in the y-direction respectively by moving at least one of these two (groups of) tomographic images in the x and y direction based on the displacement of the x direction $\Delta x = x1-x1'$ (or $x2-x2'$) and the displacement of the y-direction $\Delta y = y1-y1'$ (or $y2-y2'$) of the two (groups of) tomographic images input from the scanning region displacement calculation part 231. For example, the process for adjusting the place of the second tomographic image to the position of the first tomographic image is performed by moving the second tomographic image by $\Delta x$ in the x direction and $\Delta y$ in the y direction.

Incidentally, provided that the lengths of the scanning regions R and R' in the x direction are not equal (that is, when $x2-x1 \ne x2'-x1'$), at least one of the two (groups of) tomographic images may be configured to move based on the displacements of the x direction $\Delta x$ (min)=$x1-x1'$ and $\Delta x$ (max)=$x2-x2'$, for example, so as to allow midpoints of the x direction of the scanning regions R and R' coincident with each other. Similarly, provided that the lengths of the scanning regions R and R' in the y direction are not equal (that is, when $y2-y1 \ne y2'-y1'$), at least one of the two (groups of) tomographic images may be configured to move based on the displacements of the y direction $\Delta y$ (min)=$y1-y1'$ and $\Delta y$ (may)=$y2-y2'$, for example, so as to allow midpoints of the y direction of the scanning regions R and R' coincident with each other.

Next, the position adjustment process of images based on the displacement input from the fixation position displacement calculation part 232 is described. The image position changing part 236 adjusts the position of two (groups of) tomographic images in the x direction and in the y-direction respectively by moving at least one of these two (groups of) tomographic images in the x and y direction based on the displacement of the x direction $\Delta xf = xf-xf'$ and the displacement of the y direction $\Delta yf = yf-yf'$ of the projection position of the internal fixation target onto the fundus oculi Ef upon capturing the two (groups of) tomographic images input from the fixation position displacement calculation part 232. For example, by moving the second tomographic image by $\Delta xf$ in the x direction and by $\Delta yf$ in the y direction, the process for adjusting the position of the second tomographic image to the position of the first tomographic image is performed.

Next, the position adjustment process of images based on the displacement input from the depth position displacement calculation part 233 is described. The image position changing part 236 adjusts the position of two (groups of) tomographic images depth-wise (z direction) based on the displacement $\Delta z = z-z'$ of the coordinates at the depth position of the two (groups of) tomographic images input from the depth position displacement calculation part 233. For example, by moving the second tomographic image by $\Delta z$ in the z direction, the process for adjusting the place of the second tomographic image to the position of the first tomographic image is performed.

Next, the position adjustment process of images based on the displacement input from the accumulated image displacement calculation part 235 is described. The image position changing part 236 adjusts the position of two (groups of) tomographic images in the x direction and in the y-direction respectively by moving at least one of these two (groups of) tomographic images in the x direction and in the y-direction based on the displacement of the two accumulated images in the x direction and the y direction (indicated by $\Delta x$ and $\Delta y$ similar to the displacements of the scanning regions) based on the two (groups of) tomographic images input from the accumulated image displacement calculation part 235. For example, by moving the second tomographic image by $\Delta x$ in the x direction and $\Delta y$ in the y direction, the process for adjusting the position of the second tomographic image to the position of the first tomographic image is performed. Incidentally, when the regions of the both accumulated images are different, the position is adjusted by allowing midpoints of the x direction and of the y direction coincident with each other in similar to the case of being based on the displacement of the scanning regions.

Finally, the detailed position adjustment of (groups of) tomographic images is described. The image position changing part 236 performs calculations for the displacement so that correlation between two fundus oculi images (2-dimensional images of the surface of the fundus oculi Ef) is the highest, and the image position changing part 236 adjusts the position of two fundus oculi images based on this displacement. In addition, it is possible to extract characteristic points from each of two fundus oculi images, calculate displacements of these characteristic points, and adjust the positions of the two fundus oculi images based on these displacements. Furthermore, by using the results of the position adjustment of these two fundus oculi images, the position adjustment in the x direction and the y direction of two (groups of) tomographic images captured almost at the same time as these two fundus oculi images is performed.

It is possible to adjust the positions of the two (groups of) tomographic images more in detail by performing the position adjustment of the tomographic images based on such the position adjustment of the fundus oculi images, for example, after the (rough) position adjustment based on information of displacement input from the scanning region displacement calculation part 231 (or the fixation position displacement calculation part 232, the depth position displacement calculation part 233 or the accumulated image displacement calculation part 235).

Operation

Operations of the fundus observation device 1 having the above configuration are described with reference to FIGS. 10 to 12. These figures show an example of the operation of the fundus observation device 1 when comparing images captured on the different examination date and time in the elapsed observation of ocular affection. The operation shown in FIG. 10 relates to the case of adjusting the position of images using position information. Incidentally, the case of adjusting the position of images using accumulated images will be described later (see FIG. 12).

Position Adjustment of Images Using Position Information

First, the position adjustment of images using position information is described with reference to FIG. 10 and FIG. 11. At the beginning, on the first examination date and time, a fundus oculi image and a tomographic image (a group of tomographic images; hereinafter same as this) of the fundus oculi Ef are captured (S1). The image data 212a of the captured fundus oculi image and the image data Ga of the tomographic image are respectively stored in the image storage part 212 (S2). Incidentally, when the fundus observation device 1 is connected to a network such as LAN, the image data 212a and Ga may be stored in a database on this network.

The position information generating part 214 generates position information 213a based on information set prior to capturing the images (such as the specifying information of the scanning region R of the signal light LS and the specifying information of the fixation position) and the captured image information (S3). The generated position information 213a will be stored in the information storage part 213 (S4).

Herein, although it is sufficient that any one of the scanning region information and the fixation position information is generated as position information for the image position adjustment in the x and y direction, both information shall be generated here. In addition, also the depth information that is position information for the image position adjustment of images in the z direction shall be generated.

On the second examination date and time when a certain period (e.g., several days, several weeks, several months, several years and so on) has elapsed from the first examination date and time, a fundus oculi image and a tomographic image (a group tomographic images; hereinafter same as this) of the fundus oculi Ef are captured (S5). The image data 212b of the captured fundus oculi image and the image data Gb of the tomographic image are respectively stored in the image storage part 212 (S6).

The position information generating part 214 generates position information 213b including scanning region information, fixation position information and depth information similar to the case on the first examination date and time (S7). The generated position information 213b will be stored in the information storage part 213 (S8).

When a certain operation has been made for initiating a comparison of images of the fundus oculi Ef, the main controller 211 reads the image data 212b (or the image data 212a) of the fundus oculi image form the image storage part 212 and causes the display part 240A to display the fundus oculi image Ef' based on this image data 212b (S9).

Furthermore, the main controller 211 reads scanning region information and fixation position information of each of the position information 213a and 213b from the information storage part 213, and causes the display part 240A to display images of the scanning regions based on the two scanning region information, and images indicating the projection positions of the internal fixation target based on the two fixation position information respectively on the fundus oculi image Ef' (S10).

In addition, the main controller 211 reads the image data Gb (or the image data Ga) of the tomographic image from the image storage part 212 and causes the display part 240A to display the tomographic image Gb based on this image data (S11). This tomographic image Gb (Ga) is displayed on the display part 240A together with the fundus oculi image 212b (212a) or the like.

Figure 11:
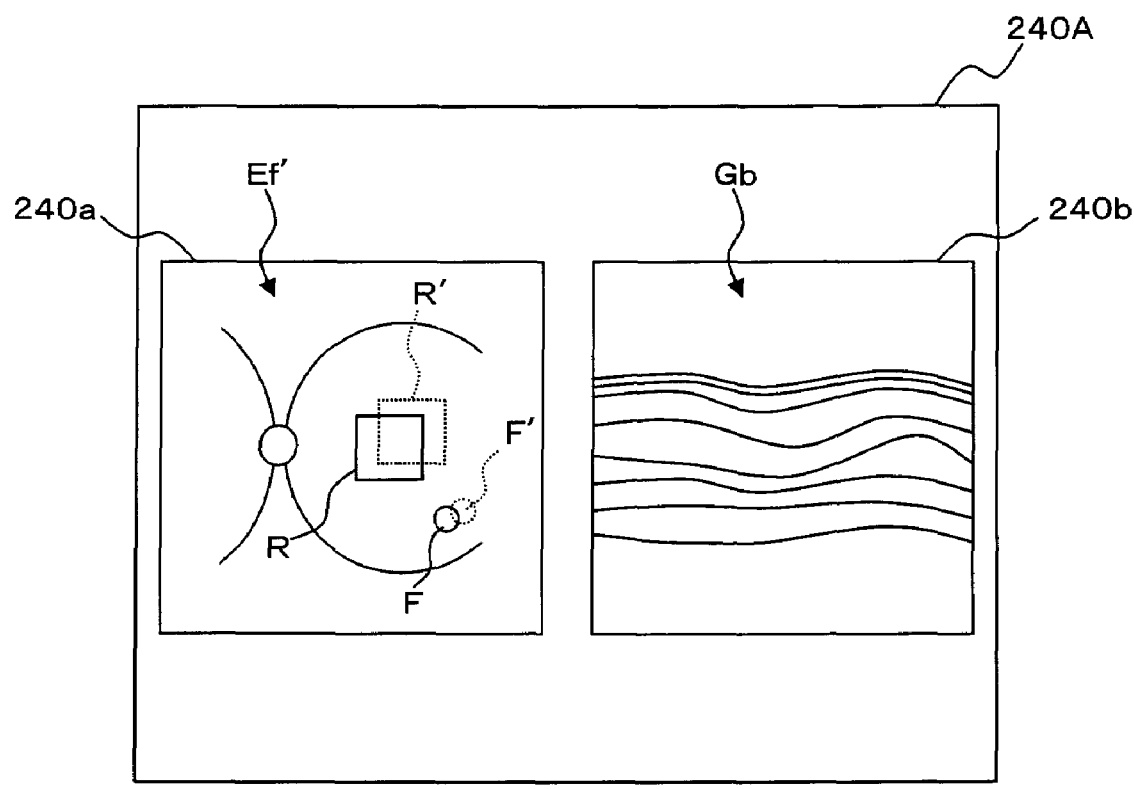
FIG. 11 is a schematic diagram showing an example of the screen displayed by a preferred embodiment of the fundus observation device related to the present invention.
Figure 12:
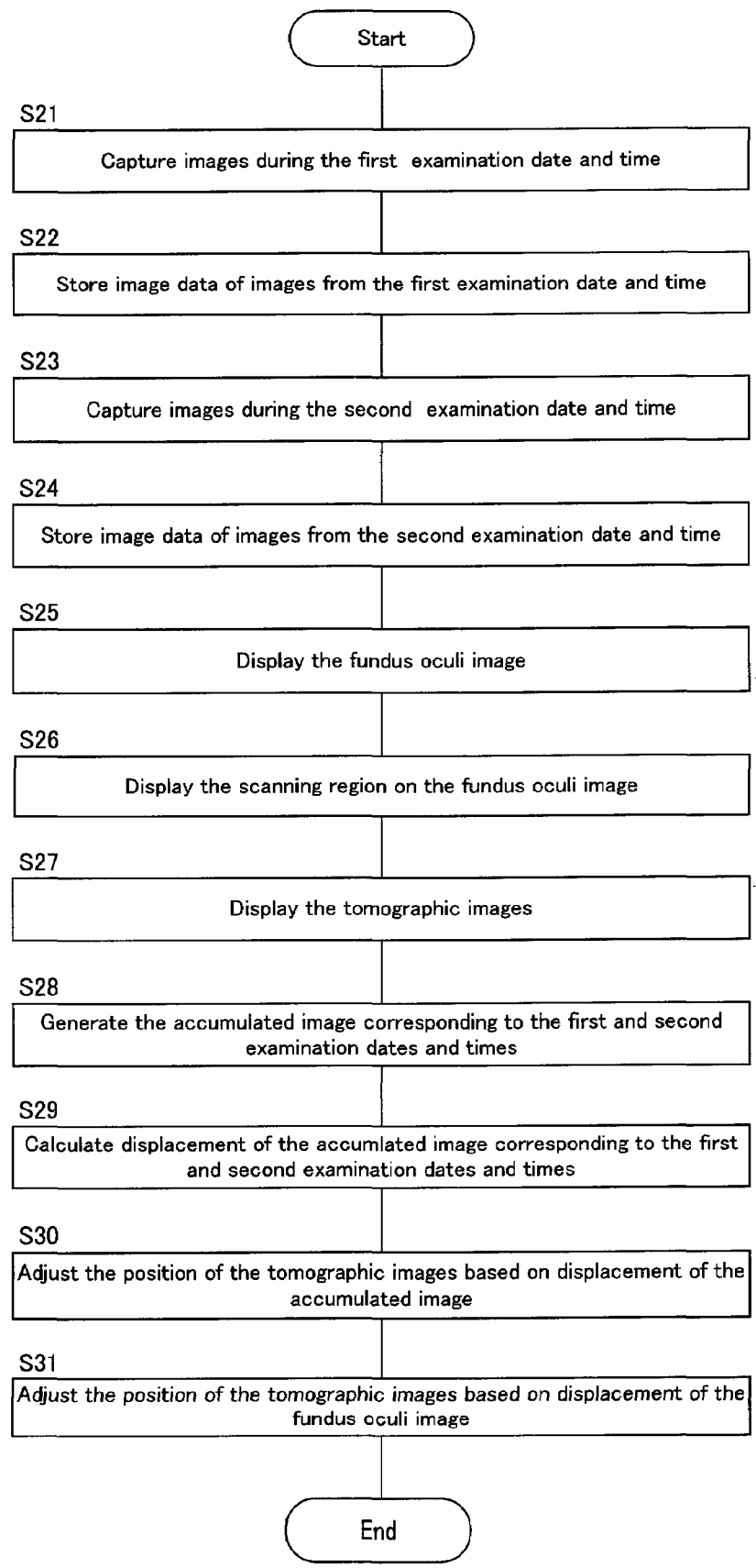
FIG. 12 is a flowchart showing one example of operation according to the preferred embodiment of the fundus observation device related to the present invention.

FIG. 11 shows one example of screens displayed on the display part 240A by step S9, S10 and S11. The display screen of the display part 240A is provided with a fundus oculi image display part 240a on which a 2-dimensional image of the surface of the fundus oculi Ef (fundus oculi image 212b) or the like is displayed and a tomographic image display part 240b on which the tomographic image Gb of the fundus oculi Ef is displayed.

Through step S9, the fundus oculi image Ef' is displayed on the fundus oculi image display part 240a. In addition, through step S11, (image indicating) the scanning region R when having captured a tomographic image on the first examination date and time and (image indicating) the scanning region R' when having captured a tomographic image on the second examination date and time are overlapped and displayed on the fundus oculi image Ef'. Furthermore, through step S10, (image indicating) the projection position F of the internal fixation target on the first examination date and time and (image indicating) the projection position F' of the internal fixation target on the second examination date and time are overlapped and displayed on the fundus oculi image Ef'.

The scanning regions R and R' and the fixation positions F and F' are displayed respectively based on the coordinates shown in the corresponding scanning region information or fixation position information. Herein, since the scanning region R' and the fixation position F' were generated at the same second examination date and time as the displayed fundus oculi image Ef', they show the position of the tomographic image Gb (that is, the position of the scanning region and the projection position of the internal fixation target) at the second examination date and time in this fundus oculi image Ef' without modification.

On the other hand, the scanning region R and the fixation position F were generated at the first examination date and time unlike the displayed fundus oculi image Ef'. Therefore, in the examinations at the first and second examination date and time, there might be misalignments of various types of conditions at the examination time, such as the misalignment of the image regions specified as scanning regions, the misalignment of the projection positions of the internal fixation target (that is, the misalignment of the photographing regions of the fundus oculi Ef), and the misalignment of the alignment of the device to an eye E. In addition, even if these conditions are coincident, for example in the case where an eye E to be examined is not fixated with certainty by the internal fixation target, there might be misalignment of the photographing regions of the fundus oculi Ef.

As a result, as shown in FIG. 11, it is usual that the scanning regions R and R' are displayed at different positions to each other and the projection positions F and F' are displayed at different positions to each other.

Incidentally, in the case of having captured plurality of tomographic images (i.e. groups of tomographic images) at the first and second examination date and time, the main controller 211 causes the tomographic image display part 240b to display one image of the groups of tomographic images Gb (Ga). As a tomographic image to be displayed, any tomographic image, for example, a tomographic image of the cross-section including the scan starting position RS or a tomographic image of the cross-section positioned in the middle in the sub scanning direction (y direction), will be selected.

The main controller 211 reads the position information 213a and 213b from the information storage part 213 and sends them to the image processing part 230, and reads the image data of the fundus oculi images 212a and 212b and the image data of tomographic images Ga and Gb from the image storage part 212 and sends them to the image processing part 230.

The scanning region displacement calculation part 231 performs calculations, based on coordinates of the region of the signal light LS shown in each of the position information 213a and 213b, for displacements of these two coordinates (in the x and y direction) (S12).

In addition, the fixation position displacement calculation part 232 performs calculations, based on coordinates of the projection position of the internal fixation target onto the fundus oculi Ef shown in each of the fixation position information of the position information 213a and 213b, for the displacements of these two coordinates (in the x and y direction) (S13).

Furthermore, the depth position displacement calculation part 233 performs calculations, based on coordinates of the depth position shown in each depth information of the position information 213a and 213b, for displacement of those two coordinates (in the z direction) (S14). The calculations for the displacement performed at the steps S12 to S14 will be input to the image position changing part 236.

The image position changing part 236 adjusts the position, by moving the tomographic image Ga at the first examination date and time and/or the tomographic image Gb at the second examination date and time in the x direction and the y direction based on the displacement of the coordinates of the scanning region of which calculation was performed at the step S12, of these two tomographic images in the x-y direction (S15).

In addition, the image position changing part 236 adjusts the position, by moving the tomographic image Ga at the first examination date and time and/or the tomographic image Gb at the second examination date and time in the x direction and the y direction based on the displacement of the coordinates of the projection position of the internal fixation target of which calculation was performed at the step S13, of these two tomographic images in the x-y direction (S16).

In addition, the image position changing part 236 adjusts the position, by moving the tomographic image Ga at the first examination date and time and/or the tomographic image Gb at the second examination date and time in the z direction based on the displacement of the depth position of the tomographic image of which calculation was performed at the step S14, of these two tomographic images in the z direction (depth-wise) (S17).

Furthermore, the image position changing part 236 performs calculations for the displacement, based on the image data 212a and 212b of the fundus oculi image, so that correlation between these two fundus oculi images is the highest, adjusts the position of these two fundus oculi images based on this displacement, and adjusts the position of the tomographic images Ga and Gb in the x and y direction by using the results of this position adjustment (S18). This is the end of the position adjustment process of tomographic images using position information.

The results of this position adjustment allows the main controller 211 to change the display position of the images R and R' of the scanning region in the fundus oculi image display part 240a and the images F and F' of the projection position of the internal fixation target. By this change of the display position, the images R and R' of the scanning region are displayed almost at the same position and the images F and F' of the projection position are displayed almost at the same position. This means that the position was adjusted between the tomographic image (the group of tomographic images) Ga at the first examination date and time and the tomographic image (the group of tomographic images) Gb at the second examination date and time.

Position Adjustment of Images Using Accumulated Images

Next, the position adjustment of images using accumulated images is described with reference to FIG. 12. At the beginning, similarly to the position adjustment using position information, a fundus oculi image and a tomographic image (a group of tomographic images; hereinafter same as this) of the fundus oculi Ef are captured on the first examination date and time (S21), and the image data 212a of the fundus oculi image and the image data Ga of the tomographic image are stored in the image storage part 212 (S22).

In addition, on the second examination date and time when a certain period has elapsed from the first examination date and time, a fundus oculi image and a tomographic image (a group of tomographic images; hereinafter same as this) of the fundus oculi Ef are captured (S23), and image data 212b of the fundus oculi image and the image data Ga of the tomographic image are stored in the image storage part 212 (S24).

Incidentally, on each of the first and second examination date and time, information indicating the scanning region of the signal light LS when capturing a tomographic image (the scanning region information described above) are generated and stored in the information storage part 213.

The main controller 211, in response to a certain operation, reads the image data 212b (or the image data 212a) of the fundus oculi image from the image storage part 212 and causes the display part 240A to display the fundus oculi image Ef' based on this image data 212b (S25) Meanwhile, the main controller 211 reads scanning region information from the information storage part 213 and causes the display part 240A to display the images indicating the scanning regions at the first and second examination date and time to overlap with the fundus oculi image Ef' (S26). Furthermore, the main controller 211 reads the image data Gb (or the image data Ga) of the tomographic image from the image storage part 212 and causes the display part 240A to display the tomographic image Gb based on this image data (S27). The displaying feature of images through the steps S25 to S27 is, for example, similar to FIG. 11 described above.

In addition, the main controller 211 reads the image data 212a and 212b of the fundus oculi image and the image data Ga and Gb of the tomographic image from the image storage part 212 and sends them to the image processing part 230. The accumulated image generating part 234 accumulates each of the image data 212a and 212b of the tomographic image depth-wise and generates an accumulated image corresponding with the first examination date and time and an accumulated image corresponding with the second examination date and time, respectively (S28). The accumulated image displacement calculation part 235 performs calculations for displacements in the x and y direction of these accumulated images corresponding with the first and second examination date and time (S29).

Next, the image position changing part 236 adjusts the position of tomographic images Ga and Gb in the x and y direction based on the displacements of the accumulated images of which calculation was performed (S30).

Furthermore, the image position changing part 236 performs calculations for the displacement so that correlation between the fundus oculi images 212a and 212b is the highest, adjusts the position of the two fundus oculi images based on this displacement, and adjusts the position of the tomographic images Ga and Gb in the x and y direction by using the results of this position adjustment (S31). In the end, the position adjustment process of tomographic images using accumulated images is completed. As a result, the main controller 211 can change the display position of the images R and R' of the scanning region in the fundus oculi image display part 240a, similarly to the case of the position adjustment of images using position information.

Incidentally, the above position adjustment by accumulated images is position adjustment in the x and y direction, so it is desirable to adjust the 3-dimensional position of tomographic images Ga and Gb by adjusting the position in the z direction with the same procedure as in the case of the position adjustment of images using position information.

EXAMPLES OF THE UTILITY OF THE POSITION ADJUSTMENT RESULTS

The results of the position adjustment of tomographic images described above can be utilized as follows in the elapsed observation of the fundus oculi Ef.

First Example of the Utility

First, one example of the displaying feature of images using the position adjustment results of tomographic images is described. Herein, at the first and second examination date and time, m tomographic images (i.e., a group of tomographic images) shall have been captured, respectively. The m tomographic images belonging to the group at the first examination date and time are indicated by symbols Ga1 to Gam, and the m tomographic images belonging to the group at the second examination date and time are indicated by symbols Gb1 to Gbm. Incidentally, even if the numbers of images belonging to the two groups are different, it is possible to process the same as follows.

The image position changing part 236 adjusts the position between the tomographic images Ga1 to Gam at the first examination date and time and the tomographic images Gb1 to Gbm at the second examination date and time. Herein, interval of adjacent tomographic images shall be equally set. That is, for each i=1 to m−1, when interval between the tomographic image Gai and the tomographic image Ga (i+1) is indicated by $\Delta da$ and interval between the tomographic image Gbi and the tomographic image Gb (i+1) is indicated by $\Delta db$, it shall be set to $\Delta da=\Delta db$.

At this time, in the tomographic image Ga1 to Gam and the tomographic image Gb1 to Gbm, for each i=1 to m, the position between the tomographic image Gai and the tomographic image Gbi are adjusted by the image position changing part 236.

The main controller 211 operates, in response to the result of this position adjustment, for each i=1 to m, so as to generate image associated information for associating the tomographic image Gai at the first examination date and time and the tomographic image Gbi at the second examination date and time. The generated image associated information is stored in, for example, the information storage part 213.

On the display screen of the display part 240A shown in FIG. 11, a display screen switching part that is not shown (consisting of a software key or the like) for switching the tomographic image to be displayed on the tomographic image display part 240b is displayed. Operation of this associated image switching part is considered as, for example, a click operation by the mouse 206 of the operating part.

The display screen switching part is provided with an identical examination image switching part for switching the display, when the tomographic image Gai at the first examination date and time (or the tomographic image Gbi at the second examination date and time) is displayed, to the other tomographic image Gaj at the first examination date and time (or the tomographic image Gbj at the second examination date and time; j≠i). When this identical examination image switching part is operated, the display will be switched to, for example, the next tomographic image Ga(i+1). In addition, it may be configured to be capable of selecting and displaying, for example, the desired one of the tomographic images Ga1 to Gam (or the tomographic images Gb1 to Gbm) (Specifically, for example, the configuration for selectably displaying a thumbnail of each tomographic image can be applied.).

Furthermore, the display screen switching part is provided with an associated image switching part for switching the display to the tomographic image associated with the displayed tomographic image. That is, when the associated image switching part is operated during the tomographic image Gai at the first examination date and time (or the tomographic image Gbi at the second examination date and time) is displayed, the display will be switched to the tomographic image Gbi at the second examination date and time associated with this tomographic image Gai (or the tomographic image Gai at the first examination date and time associated with this tomographic image Gbi).

A user can display a tomographic image Gai (or tomographic image Gbi) of the desired cross-section by operating the identical examination image switching part. Furthermore, the user can display a tomographic image Gbi (or tomographic image Gai) associated with this tomographic image Gai (or tomographic image Gbi) by operating the associated image switching part. In addition, the user can display the tomographic image Gai again by operating the associated image switching part again. By switching the display image in this way, it is possible to alternately display the tomographic image Gai and the tomographic image Gbi almost at the same cross-section position, so it is possible to easily compare temporal changes in the state of the cross-section potion (e.g. the thickness of retina).

As a modification of this displaying feature, it is also possible to configure to display plurality of tomographic image display parts 240b simultaneously, display the tomographic image Gai on the one of them, and display the tomographic image Gbi on the other. Furthermore, it is also able to constitute to, in response to the tomographic image displayed on one tomographic image display part 240b having been switched by the identical examination image switching part, display the tomographic image associated with that tomographic image on the other tomographic image display part 240b.

Second Example of the Utility

Next, one example of the image analysis processing using the position adjustment results of tomographic images are described. In the elapsed observation, various indicators related to the state of the fundus oculi may be analyzed. As one example of these indicators, for example, there is the thickness of the retina. The thickness of the retina can be obtained, for example, by performing calculations for difference between the z coordinate value of the retina surface and the z coordinate value of the retinal pigment epithelium layer in the tomographic image.

Assume that, for each i=1 to m, the tomographic image Gai at the first examination date and time and the tomographic image Gbi at the second examination date and time are associated with each other. At this time, the main controller 211 performs calculations for the thickness of the retina at that cross-section position based on each tomographic image Gai and performs calculations for the thickness of the retina at that cross-section position based on each tomographic image Gbi.

Furthermore, the main controller 211, for each cross-section position (i.e. for each i=1 to m), performs calculations for the difference between the thickness of the retina based on the tomographic image Gai and the thickness of the retina based on the tomographic image Gbi. As a result, the distribution of temporal changes in the thickness of the retina for each cross-section position can be obtained. The main controller 211 can cause the display part 240A to display the image in which the obtained distribution is expressed, for example, by gradation (distributed image). A user can easily figure out the distribution state of temporal changes in the thickness of the retina in the fundus oculi Ef by seeing this distribution image.

Action and Effect

The action and effect of the fundus observation device 1 as above is explained. This fundus observation device 1 generates, for the fundus oculi image 212a and the tomographic image Ga captured at the first examination date and time, the position information 213a indicating the position of the tomographic image Ga in the fundus oculi image 212a, and generates, for the fundus oculi image 212b and the tomographic image Gb captured at the second examination date and time, the position information 213b indicating the position of the tomographic image Gb in the fundus oculi image 212b. And then, based on these position information 213a and 213b, the fundus observation device 1 operates to adjust the position between the tomographic image Ga at the first examination date and time and the tomographic image Gb at the second examination date and time.

More specifically, the fundus observation device 1 operates to adjust the position between the tomographic images Ga and Gb in the direction of the surface of the fundus oculi Ef (x-y direction) by using the scanning region information and the fixation position information included in the position information 213a and 213b. In addition, it is also able to adjust the position in the x-y direction based on the position adjustment results of the accumulated image of each tomographic image Ga and Gb. Furthermore, it also operates to adjust the position between the tomographic images Ga and Gb depth-wise of the fundus oculi Ef (z direction) by using the depth information included in the position information 213a and 213b. By combining such position adjustment processes, a 3-dimensional position can be adjusted.

In addition, the fundus observation device 1 operates to adjust the position between the fundus oculi image 212a at the first examination date and time and the fundus oculi image 212b at the second examination date and time, and adjusts the detailed position between the tomographic images Ga and Gb in the x-y direction based on the results thereof.

As described above, according to the fundus observation device 1 related to the present embodiment, it is possible to preferably adjust the position between the tomographic images Ga and Gb of the fundus oculi Ef for which examination date and time differ, so it is possible to effectively and efficiently perform the elapsed observation using tomographic images of the fundus oculi Ef.

Modified Example

The configuration described above is merely one example to preferably implement the fundus observation device related to the present invention. Therefore, optional modifications may be implemented appropriately within the scope of the present invention.

Although the fundus observation device 1 related to the above embodiment is constituted to be capable of adjusting the position of the tomographic images of the fundus oculi based on each of the scanning region information, the fixation position information, the depth information and the accumulated image, it is sufficient to be configured to be capable of adjusting the position based on one or more of these four items.

In particular, for the position adjustment of the fundus oculi in the x-y direction, it is sufficient to be designed for operation based on any one of the scanning region information, the fixation position information and the accumulated image. Incidentally, when the position is adjusted based on only the accumulated image, it is sufficient to provide with only the configuration as a optical image measuring device (OCT device).

For the position adjustment of tomographic images of the fundus oculi, it is desired to improve the accuracy of the position adjustment by adjusting the 3-dimensional position in the x direction, y direction and z direction with combining the position adjustment in the x-y direction based on the scanning region information, the fixation position information, or the accumulated image and the position adjustment in the z direction based on the depth information.

In the above embodiment, the position adjustment processing of two tomographic images that have already been captured, but the configuration of the above embodiment can be applied to capture tomographic images of (almost) the same site as a past examination. For that purpose, for example, based on the fixation position information in the past examination, the LCD 140 is controlled to display the internal fixation target at the same position as in the past examination and the eye is fixated in the same direction as in the past examination. Furthermore, the current fundus oculi image is displayed and the image indicating the scanning region based on the scanning region information in the past examination is displayed overlapped with that fundus oculi image. At this time, the calculations for the displacement between the fundus oculi image in the past examination and the current fundus oculi image is performed (e.g., the displacement for adjusting the position is calculated so that the correlation is the highest), and the scanning region in the past examination is displayed at the position moved depending on this displacement. The position of this displayed scanning region is specified as the scanning region of the signal light LS in the examination at this time. As a result, the same scanning region as in the past examination can be specified. Incidentally, fundus oculi images or scanning regions do not necessarily have to be displayed.

The fundus observation device according to the present embodiment has a retinal camera (unit) as a device that forms two-dimensional images of the fundus oculi surface, while it may have a configuration in which a two-dimensional image of the fundus oculi surface is formed using arbitrary ophthalmological equipment such as a slit lamp biomicroscope, for example.

Moreover, in the above embodiment, the image forming process is performed by the image forming part 220 (image forming board 208) and each controlling process are operated by the controlling part 210 (microprocessor 201, etc.), but it can be configured to operate these two processes by one or several computers.

Advantages

With the fundus observation device according to the embodiment, a fundus observation device comprising: image forming part including a first image forming part configured to form a 2-dimensional image of the surface of the fundus oculi of an eye and a second image forming part configured to form tomographic images of said fundus oculi, a position information generating part configured to generate position information for said 2-dimensional image and said tomographic image generally formed simultaneously, indicating the position of the tomographic image in the 2-dimensional image, an image processing part configured to adjust the position, based on said position information generated for said 2-dimensional image and said tomographic image generally formed simultaneously at first and based on said position information generated for said 2-dimensional image and said tomographic image generally formed simultaneously at a subsequent time, of said former tomographic image and said latter tomographic image. Thus, according to the embodiment, the position of the former tomographic image and the latter tomographic image for which examination dates and times differ can preferably be adjusted, so it is possible to effectively and efficiently perform the elapsed observation using tomographic images of a fundus oculi Ef.

Also, with the fundus observation device according to the embodiment, a fundus observation device comprising: an image forming part configured to form a tomographic image of a fundus oculi of an eye, a position information generating part configured to generate the depth information indicating the position of the tomographic image depth-wise based on the formed tomographic image, and an image processing part configured to adjust the position, based on said depth information generated for said tomographic image formed in first and said depth information generated for said tomographic image formed at a subsequent time, of said former tomographic image and said latter tomographic image depth-wise. Thus, according to the embodiment, the positions of the former tomographic image and the latter tomographic image for which examination dates and times differ depth-wise can preferably be adjusted, so it is possible to effectively and efficiently perform the elapsed observation using tomographic images of a fundus oculi.

Also, with the fundus observation device according to the embodiment, a fundus observation device comprising: an image forming part configured to form a tomographic image of a fundus oculi of an eye, an accumulated image generating part configured to generate a first and a second accumulated images by accumulating each of a first said tomographic image and a second said tomographic image formed on different examination dates and times depth-wise, an accumulated image displacement calculating part configured to perform calculations for displacement of the generated first accumulated image and second accumulated image, and an image position changing part configured to adjust the position, based on the displacement of which calculation was performed, of said first tomographic image and said second tomographic image in the direction of the surface of said fundus oculi. Thus, according to the embodiment, the positions of the first tomographic image and the second tomographic image for which examination dates and times differ in the direction of the surface of the fundus oculi can preferably be adjusted, so it is possible to effectively and efficiently perform the elapsed observation using tomographic images of a fundus oculi Ef.

What is claimed is:

1. A fundus observation device comprising:
    an image forming part configured to form a group of tomographic images of said fundus oculi for respective depths based on data captured by an optical scan;
    an accumulation part configured to accumulate the tomographic images for respective depths in order to generate an accumulation image that is a planar image:
        a position information generating part configured to generate position information indicating the position of the accumulation image in the fundus oculi; and
        an image processing part configured to adjust the position, based on said position information generated in advance and based on said position information generated at a subsequent time, of former tomographic images and latter tomographic images, respectively.

2. A fundus observation device according to claim 1, wherein said image forming part comprises:
    a light source; an interference light generator to split said light emitted from said light source into the signal light directed toward said fundus oculi and the reference light directed toward a reference object and to generate interference light by superposing the signal light having reached said fundus oculi and the reference light having reached said reference object; a detector to receive the generated interference light and to output a detecting signal; and a scanner to scan the incident position of said signal light to said fundus oculi respectively in a certain main scanning direction and in a sub scanning direction perpendicular to the main scanning direction,
    wherein, for each of a plurality of said incident positions along said main scanning direction, an image depth-wise of said fundus oculi is formed at the incident position based on said detecting signal based on the interference light generated from the signal light having reached the incident position and said reference light, and a tomographic image along said main scanning direction is formed based on the images depth-wise formed for said plurality of incident positions so that said tomographic image is formed at each of two or more positions along said sub scanning direction,
    wherein said position information generating part expresses as said position information the region in which said signal light was scanned by said scanner when said tomographic image was formed, said position information expressed in coordinates of a 2-dimensional coordinate system, and
    wherein said image processing part includes a displacement calculating part to perform calculations for displacement between said each coordinate when said two or more former tomographic images were formed and said each coordinate when said two or more latter tomographic images were formed, and said image processing part adjusts the position, based on the displacement of which calculation was performed, of said former tomographic image and said latter tomographic image in the direction of the surface of said fundus oculi.

3. A fundus observation device according to claim 1, wherein said image forming part includes a fixation target projecting part to project on said fundus oculi a fixation target to have said eye fixated,
    said position information generating part expresses the projection position of said fixation target as said position information in coordinates of a 2-dimensional coordinate system, and
    said image processing part includes a displacement calculating part configured to perform calculations for displacement between said coordinate when said former tomographic images were formed and said coordinate when said latter tomographic images were formed and said image processing part adjusts the position, based on the displacement for which calculation was performed, of said former tomographic image and said latter tomographic image in the direction of the surface of said fundus oculi.

4. A fundus observation device according to claim 1, wherein said position information generating part generates depth information as said position information, the depth information indicating depth-wise position of the tomographic image based on the tomographic image formed by said image forming part, and
    said image processing part adjusts the position of said former tomographic image and said latter tomographic image depth-wise, based on said depth information generated for said former tomographic image and said depth information generated for said latter tomographic image.

5. A fundus observation device according to claim 4, wherein said depth information includes information that the position of a certain layer of a fundus oculi in the tomographic image formed by said image forming part is expressed in coordinates preset on said tomographic image, and said image processing part adjusts the depth-wise position of said former tomographic image and said latter tomographic image, so as to match said coordinates corresponding with said former tomographic image and the coordinates corresponding with said latter tomographic image.

6. A fundus observation device comprising:
   an image forming part configured to form a group of tomographic images of a fundus oculi of an eye for respective depths based on data captured by an optical scan;
   an accumulated image generating part configured to generate a first and a second accumulated images that are planar images by accumulating tomographic images for respective depths for each of a first group of tomographic images and a second group of tomographic images formed on different examination dates and times;
   an accumulated image displacement calculating part configured to perform calculations for displacement of the generated first accumulated image and second accumulated image; and
   an image position changing part configured to adjust the position, based on the calculated displacement, of said first group of tomographic images and said second group of tomographic images in the direction of the surface of said fundus oculi.

7. A fundus observation device according to claim 6, wherein said image forming comprises:
   said light source; an interference light generator to split light emitted from the light source into the signal light directed toward said fundus oculi and the reference light directed toward a reference object and to generate interference light by superposing the signal light having reached said fundus oculi and the reference light having reached said reference object; a detector to receive the generated interference light and to output a detecting signal; and a scanner to scan the incident position of said signal light to said fundus oculi respectively in a certain main scanning direction and in a sub scanning direction perpendicular to the main scanning direction,
   wherein, for each of a plurality of said incident position along said main scanning direction, an image depth-wise of said fundus oculi at the incident position is formed based on said detecting signal based on the interference light generated from the signal light having reached the incident position and said reference light, and a tomographic image along said main scanning direction is formed based on the images depth-wise formed for said plurality of incident positions so that said tomographic image is formed at each of two or more positions along said sub scanning direction, in order to generate a first and a second accumulation images, and
   wherein said accumulated image generating part generates said first accumulated image by accumulating tomographic images of the first group for respective depths and generates said second accumulated image by accumulating tomographic images of the second group for respective depths.

* * * * *